US010172929B2

(12) United States Patent
Monath et al.

(10) Patent No.: US 10,172,929 B2
(45) **Date of Patent: *Jan. 8, 2019**

(54) FLAVIVIRUS VACCINES

(71) Applicant: Sanofi Pasteur Biologics, LLC, Cambridge, MA (US)

(72) Inventors: Thomas P. Monath, Harvard, MA (US); Farshad Guirakhoo, Melrose, MA (US); Juan Arroyo, Rockville, MD (US); Konstantin V. Pugachev, Natick, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,319

(22) Filed: Oct. 6, 2014

(65) Prior Publication Data

US 2015/0024004 A1 Jan. 22, 2015

Related U.S. Application Data

(63) Continuation of application No. 13/668,819, filed on Nov. 5, 2012, now Pat. No. 8,852,914, which is a continuation of application No. 13/423,746, filed on Mar. 19, 2012, now abandoned, which is a continuation of application No. 13/198,976, filed on Aug. 5, 2011, now abandoned, which is a continuation of application No. 12/962,216, filed on Dec. 7, 2010, now abandoned, which is a continuation of application No. 12/325,864, filed on Dec. 1, 2008, now abandoned, which is a continuation of application No. 10/345,036, filed on Jan. 15, 2003, now Pat. No. 7,459,160.

(60) Provisional application No. 60/385,281, filed on May 31, 2002, provisional application No. 60/348,949, filed on Jan. 15, 2002.

(51) Int. Cl.

| | |
|---|---|
| ***A61K 39/12*** | (2006.01) |
| ***C07K 14/005*** | (2006.01) |
| ***C07K 7/00*** | (2006.01) |
| ***C12N 7/00*** | (2006.01) |
| *A61K 39/00* | (2006.01) |

(52) U.S. Cl.

CPC ............ *A61K 39/12* (2013.01); *C07K 14/005* (2013.01); *C12N 7/00* (2013.01); *A61K 2039/5254* (2013.01); *C12N 2770/24122* (2013.01); *C12N 2770/24134* (2013.01); *C12N 2770/24162* (2013.01); *Y02A 50/386* (2018.01); *Y02A 50/388* (2018.01); *Y02A 50/39* (2018.01); *Y02A 50/394* (2018.01)

(58) Field of Classification Search

None

See application file for complete search history.

(56) References Cited

U.S. PATENT DOCUMENTS

| | | | |
|---|---|---|---|
| 6,136,561 | A | 10/2000 | Ivy et al. |
| 6,171,854 | B1 | 1/2001 | Galler et al. |
| 6,184,024 | B1 | 2/2001 | Lai et al. |
| 6,416,763 | B1 | 7/2002 | McDonell et al. |
| 6,682,883 | B1 | 1/2004 | Monath et al. |
| 6,696,281 | B1 | 2/2004 | Chambers et al. |
| 6,878,372 | B2 | 4/2005 | Monath et al. |
| 7,459,160 | B2 | 12/2008 | Monath et al. |
| 2003/0044773 | A1 | 3/2003 | Kleanthous et al. |
| 2003/0194801 | A1 | 10/2003 | Bonaldo et al. |
| 2004/0223979 | A1 | 11/2004 | Chambers et al. |
| 2004/0259224 | A1 | 12/2004 | Guirakhoo |
| 2005/0002968 | A1 | 1/2005 | Monath et al. |
| 2005/0053624 | A1 | 3/2005 | Arroyo et al. |
| 2007/0184469 | A1 | 8/2007 | Depres et al. |
| 2009/0191240 | A1 | 7/2009 | Monath et al. |

FOREIGN PATENT DOCUMENTS

| | | |
|---|---|---|
| WO | WO 93/06214 | 4/1993 |
| WO | WO 98/37911 | 9/1998 |
| WO | WO 01/39802 | 7/2001 |
| WO | WO 02/072835 | 9/2002 |
| WO | WO 02/102828 | 12/2002 |
| WO | WO 03/063725 | 8/2003 |
| WO | WO 03/101397 | 12/2003 |
| WO | WO 03/103571 | 12/2003 |
| WO | WO 04/045529 | 6/2004 |
| WO | WO 05/040390 | 5/2005 |
| WO | WO 05/049815 | 6/2005 |
| WO | WO 05/082020 | 9/2005 |
| WO | WO 06/044857 | 4/2006 |
| WO | WO 06/116182 | 11/2006 |
| WO | WO 07/051267 | 5/2007 |

OTHER PUBLICATIONS

U.S. Appl. No. 08/807,445, filed Feb. 28, 1997, Chambers et al.
U.S. Appl. No. 09/007,664, filed Jan. 15, 1998, Chambers et al.
U.S. Appl. No. 09/121,587, filed Jul. 23, 1998, Chambers et al.
U.S. Appl. No. 09/452,638, filed Dec. 1, 1999, Chambers et al.
U.S. Appl. No. 10/701,122, filed Nov. 4, 2003, Chambers et al.
U.S. Appl. No. 12/423,566, filed Apr. 14, 2009, Chambers et al.
U.S. Appl. No. 12/592,529, filed Nov. 30, 2009, Chambers et al.
Aihara et al., "Identification of Mutations That Occurred on the Genome of Japanese Encephalitis Virus During the Attenuation Process," Virus Genes 5: 95-109, 1991.
Allison et al., "Mapping of Functional Elements in the Stem-Anchor Region of Tick-Borne Encephalitis Virus Envelope Protein E," J. Virol. 73:5605-5612, 1999.
Allison et al., "Mutational Evidence for an Internal Fusion Peptide in Flavivirus Envelope Protein E," J. Virol. 75:4268-4275, 2001.
Arroyo et al., "ChimeriVax-West Nile Virus Live-Attenuated Vaccine: Preclinical Evaluation of Safety, Immunogenicity, and Efficacy," J. Virol. 78:12497-12507, 2004.
Arroyo et al., "Yellow Fever Vector Live-Virus Vaccines: West Nile Virus Vaccine Development," Trends Mol. Med. 7:350-354, 2001.
Arroyo et al., "Molecular Basis for Attenuation of Neurovirulence of a Yellow Fever Virus/Japanese Encephalitis Virus Chimera Vaccine (ChimeriVax-JE)," J. Virol. 75:934-942, 2001.

(Continued)

*Primary Examiner* — Stacy Brown Chen

(74) *Attorney, Agent, or Firm* — Clark & Elbing LLP

(57) ABSTRACT

The invention provides flavivirus vaccines and methods of making and using these vaccines.

27 Claims, 7 Drawing Sheets

(56) References Cited

OTHER PUBLICATIONS

Bancroft, "Current Status of Dengue Vaccines and Prospects for the Future," *Puerto Rico Health Sci. J.* 6:23-26, 1987. Abstract only.
Barrett, "Current Status of Flavivirus Vaccines," Ann. N. Y. Acad. Sci. 951:262-271, 2001.
Bonaldo et al., "The Yellow Fever 17D Vaccine Virus as a Vector for the Expression of Foreign Proteins: Development of New Live Flavivirus Vaccines," Mem. Inst. Oswaldo Cruz, Rio de Janeiro 95(Suppl. 1):215-223, 2000.
Bonaldo et al., "Surface Expression of an Immunodominant Malaria Protein B Cell Epitope by Yellow Fever Virus," J. Mol. Biol. 315:873-885, 2002.
Bonaldo et al., "Attenuation of Recombinant Yellow Fever 17D Viruses Expressing Foreign Protein Epitopes at the Surface," J. Virol. 79:8602-8613, 2005.
Bonaldo et al., "Expression of Foreign Protein Epitopes at the Surface or Recombinant Yellow Fever 17D Viruses Based on Three-Dimensional Modeling of Its Envelope Protein," Cell Biochem. Biophys. 44:313-324, 2006.
Bray et al., "Construction of Intertypic Chimeric Dengue Viruses by Substitution of Structural Protein Genes," Proc. Natl. Acad. U.S.A. 88:10342-10346, 1991.
Bray et al., "Genetic Determinants Responsible for Acquisition of Dengue Type 2 Virus Mouse Neurovirulence," J. Virol. 72:1647-1651, 1998.
Cardosa, "Dengue Vaccine Design: Issues and Challenges," British Med. Bull. 54:395-405, 1998.
Carle et al., "Experiments on the Transmission of an Icterogenic Agent in Yellow Fever Vaccine to Horses and Swine," J. Bacteriol. 48:45-69, 1944.
Caufour et al., "Construction, Characterization and Immunogenicity of Recombinant Yellow Fever 17D-Dengue Type 2 Viruses," Virus Res. 1-14, 2001.
Chambers et al., "Mutagenesis of the Yellow Fever Virus NS2B/3 Cleavage Site: Determinants of Cleavage Site Specificity and Effects on Polyprotein Processing and Viral Replication," J. Virol. 1600-1605, 1995.
Chambers et al., "Vaccine Development Against Dengue and Japanese Encephalitis: Report of a World Health Organization Meeting," Vaccine 15:1494-1502, 1997.
Chambers et al., "Yellow Fever/Japanese Encephalitis Chimeric Viruses: Construction and Biological Properties," J. Virol. 73:3095-3101, 1999.
Chen et al., "Generation and Characterization of Organ-Tropism Mutants of Japanese Encephalitis Virus in Vivo and in Vitro," Virology 223:79-88, 1996.
Coia et al., "Nucleotide and Complete Amino Acid Sequences of Kunjin Virus: Definitive Gene Order and Characteristics of the Virus-Specified Proteins," J. Gen. Virol. 69:1-21, 1988.
Davis et al., "West Nile Virus Recombinant DNA Vaccine Protects Mouse and Horse from Virus Challenge and Expresses In Vitro a Noninfectious Recombinant Antigen That Can be Used in Enzyme-Linked Immunosorbent Assays," J. Virol. 75:4040-4047, 2001.
Dermime et al., "Vaccine and Antibody-Directed T Cell Tumour Immunotherapy," Biochim. Biophys. Acta 1704:11-35, 2004.
De Vries et al., "Genetic Manipulation of Equine Arteritis Virus Using Full-Length cDNA Clones: Separation of Overlapping Genes and Expression of a Foreign Epitope," Virology 270:84-97, 2000.
dos Santos et al., "Determinants in the Envelope E Protein and Viral RNA Helicase NS3 that Influence the Induction of Apoptosis in Response to Infection with Dengue Type 1 Virus," Virology 274:292-308, 2000.
Duarte dos Santos et al., "Complete nucleotide sequence of yellow fever virus vaccine strains 17DD and 17D-213," Virus Res. 35:35-41, 1995.
Edelman et al., "Phase I Trial of 16 Formulations of a Tetravalent Live-Attenuated Dengue Vaccine," Am. J. Trop. Med. Hyg. 69(Suppl 6):48-60, 2003.
Galler et al., "The Yellow Fever 17D Vaccine Virus: Molecular Basis of Viral Attenuation and its Use as an Expression Vector," Braz. J. Biol. Res. 30:157-168, 1997.
Galler et al., "Genetic Variability Among Yellow Fever Virus 17D Substrains," Vaccine 16:1-5, 1998.
Goryshin et al., "Tn5 In Vitro Transposition," J. Biol. Chem. 273:7367-7374, 1998.
Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate Against Japanese Encephalitis," Virology 257:363-372, 1999.
Guirakhoo et al., "Recombinant Chimeric Yellow Fever-Dengue Type 2 Virus is Immunogenic and Protective in Nonhuman Primates," J. Virol. 74:5477-5485, 2000.
Guirakhoo et al., "Construction, Viremia, and Immunogenicity Profile of Recombinant Chimeric Yellow Fever/Dengue Viruses in Nonhuman Primates," Program and Abstracts of the 49$^{th}$ Annual Meeting of the American Society of Tropical Medicine and Hygiene, Houston, Texas, Oct. 29-Nov. 2, 2000, Supplement to Am. J. Trop. Med. Hyg. 313, Abstract.
Guirakhoo et al., "Construction, Viremia, and Immunogenicity Profile of Recombinant Chimeric Yellow Fever/Dengue Viruses in Nonhuman Primates," Program and Abstracts of the 49$^{th}$ Annual Meeting of the American Society of Tropical Medicine and Hygiene, Houston, Texas, Oct. 29-Nov. 2, 2000, Supplement to Am. J. Trop. Med. Hyg. 1722, Abstract.
Guirakhoo et al., "Construction, Safety, and Immunogenicity in Nonhuman Primates of a Chimeric Yellow Fever-Dengue Virus Tetravalent Vaccine," J. Virol. 75:7290-7304, 2001.
Guirakhoo et al., "Development of ChimeriVax™—Yellow Fever Based Vaccines for Dengue and Japanese Encephalitis Viruses," 6$^{th}$ International Symposium on Positive Strand RNA Viruses, Paris, May 28-Jun. 2, 2001, Abstract.
Guirakhoo et al., "Viremia and Immunogenicity in Nonhuman Primates of a Tetravalent Yellow Fever—Dengue Chimeric Vaccine: Genetic Reconstructions, Dose Adjustment, and Antibody Responses Against Wild-Type Dengue Virus Isolates," Virology 298:146-159, 2002.
Guirakhoo et al., "Safety and Efficacy of Chimeric Yellow Fever—Dengue Virus Tetravalent Vaccine Formulations in Nonhuman Primates," J. Virol. 78:4761-4775, 2004.
Guirakhoo et al., "A Single Amino Acid Substitution in the Envelope Protein of Chimeric Yellow Fever—Dengue 1 Vaccine Virus Reduces Neurovirulence for Suckling Mice and Viremia/Viscerotropism for Monkeys," J. Virol. 78:9998-10008, 2004.
Guirakhoo et al., "Live Attenuated Chimeric Yellow Fever Dengue Type 2 (ChimeriVax™-DEN2) Vaccine: Phase I Clinical Trial for Safety and Immunogenicity," Human Vaccines 2:60-67, 2006.
Guy et al., "Evaluation by Flow Cytometry of Antibody-Dependent Enhancement (ADE) of Dengue Infection by Sera from Thai Children Immunized with a Live-Attenuated Tetravalent Dengue Vaccine," Vaccine 22:3563-3574, 2004.
Halstead et al., "Rapid Review: The Future of Dengue Vaccines," The Lancet 360:1243-1245, 2002.
Hurrelbrink et al., "Attenuation of Murray Valley Encephalitis Virus by Site-Directed Mutagenesis of the Hinge and Putative Receptor-Binding Regions of the Envelope Protein," J. Virol. 75:7692-7702, 2001.
Innis et al., "Progress in Development of a Live-Attenuated, Tetravalent Dengue Virus Vaccine by the United States Army Medical Research and Materiel Command," Am. J. Trop. Med. Hyg. 69(Suppl 6):1-4, 2003.
Johnson et al., "Growth Characteristics of Chimerivax™-Den2 Vaccine Virus in *Aedes aegypti* and *Aedes albopictus* Mosquitoes," Am. J. Trop. Med. Hyg. 67:260-265, 2002.
Kanesa-thasan et al., "Safety and Immunogenicity of Attenuated Dengue Virus Vaccines (Aventis Pasteur) in Human Volunteers," Vaccine 19:3179-3188, 2001.
Kolaskar et al., "Prediction of Three-Dimensional Structure and Mapping of Conformational Epitopes of Envelope Glycoprotein of Japanese Encephalitis Virus," Virology 261:31-42, 1999.

(56) References Cited

OTHER PUBLICATIONS

Kurane et al., "Immunity and Immunopathology in Dengue Virus Infections," Sem. Immunol. 4:121-127, 1992. Abstract only.
Lai et al., "Evaluation of Molecular Strategies to Develop a Live Dengue Vaccine," Clin. Diag. Virol. 10:173-179, 1998.
Lai et al., "Chimeric Flaviviruses: Novel Vaccines Against Dengue Fever, Tick-Borne Encephalitis, and Japanese Encephalitis," Adv. Virus Res. 61:469-509, 2003.
Laoprasopwattana et al., "Dengue Virus (DV) Enhancing Antibody Activity in Preillness Plasma does not Predict Subsequent Disease Severity or Viremia in Secondary DV Infection," J. Infect. Dis. 192:510-519, 2005. Erratum in *J. Infect. Dis.* 192:1863, 2005.
Lee et al., "Changes in the Dengue Virus Major Envelope Protein on Passaging and Their Localization on the Three-Dimensional Structure of the Protein," Virology 232:281-290, 1997.
Lee et al,, "Mechanism of Virulence Attenuation of Glycosaminoglycan-Binding Variants of Japanese Encephalitis Virus and Murray Valley Encephalitis Virus," J. Virol. 76:4901-4911, 2002.
Li et al., "Chimeric Influenza Virus Induces Neutralizing Antibodies and Cytotoxic T Cells Against Human Immunodeficiency Virus Type 1," J. Virol. 67:6659-6666, 1993.
Mandl et al., "Sequence of the Genes Encoding the Structural Proteins of the Low-Virulence Tick-Borne Flaviviruses Langat TP21 and Yelantsev," Virology 185:891-895, 1991.
Mandl et al., "Complete Genomic Sequence of Powassan Virus: Evaluation of Genetic-Elements in Tick-Borne Versus Mosquito-Borne Flaviviruses," Virology 194:173-184, 1993.
Mandl et al., "Attenuation of Tick-Borne Encephalitis Virus by Structure-Based Site-Specific Mutagenesis of a Putative Flavivirus Receptor Binding Site," J. Virol. 74:9601-9609, 2000.
Mandl et al., "Adaptation of Tick-Borne Encephalitis Virus to BHK-21 Cells Results in the Formation of Multiple Heparan Sulfite Binding Sites in the Envelope Protein and Attenuation In Vivo," J. Virol. 75:5627-5637, 2001.
Marchevsky et al., "Phenotypic Analysis of Yellow Fever Virus Derived from Complementary DNA," Am. J. Trop. Med. Hyg. 52:75-80, 1995.
McAllister et al., "Recombinant Yellow Fever Viruses are Effective Therapeutic Vaccines for Treatment of Murine Experimental Solid Tumors and Pulmonary Metastases," J. Virol. 74:9197-9205, 2000.
McMinn, "The Molecular Basis of Virulence of the Encephalitogenic Flaviviruses," J. Gen. Virol. 78:2711-2722, 1997.
Modis et al., "A Ligand-Binding Pocket in the Dengue Virus Envelope Glycoprotein," Proc. Natl. Acad. Sci. U.S.A. 100:6986-6991, 2003.
Monath et al., "Recombinant, Chimaeric Live, Attenuated Vaccine (ChimerVax™) Incorporating the Envelope Genes of Japanese Encephalitis (SA14-14-2) Virus and the Capsid and Nonstructural Genes of Yellow Fever (17D) Virus is Safe, Immunogenic and Protective in Non-Human Primates," Vaccine 17:1869-1882, 1999.
Monath, "Molecular Distinctions Between Attenuated (Vaccine) and Virulent Yellow Fever Viruses," In, Plotkin SA and Orenstein WA (eds). Vaccines, 3rd edition, Saunders (Philadelphia), pp. 815-879, 1999.
Monath et al., "Chimeric Yellow Fever Virus 17D—Japanese Encephalitis Virus Vaccine: Dose-Response Effectiveness and Extended Safety Testing in Rhesus Monkeys," J. Virol. 74:1742-1751, 2000.
Monath et al., "Yellow Fever 17D as a Vector for Vaccines Against Heterologous Flaviviruses," American Society for Virology, 19th Annual Meeting, Colorado State University, Fort Collins, Colorado, Jul. 8-12, 2000, Abstract W17-7, p. 85.
Monath, "Prospects for Development of a Vaccine Against the West Nile Virus," Ann. N.Y. Acad. Sci. 951:1-12, 2001.
Monath et al., "West Nile Virus Vaccine," Curr. Drug Targets Infect. Disord. 1:1-14, 2001.
Monath, "Yellow Fever: an Update," Lancet Infect. Dis. 1:11-20, 2001.
Monath et al., "Single Mutation in the Flavivirus Envelope Protein Hinge Region Increases Neurovirulence for Mice and Monkeys but Decreases Viscerotropism for Monkeys: Relevance to Development and Safety Testing of Live, Attenuated Vaccines," J. Virol. 76:1932-1943, 2002.
Monath et al., "Clinical Proof of Principle for ChimeriVax™: Recombinant Live, Attenuated Vaccines Against Flavivirus Infections," Vaccine 20:1004-1018, 2002.
Morens et al,, "Measurement of Antibody-Dependent Infection Enhancement of Four Dengue Virus Serotypes by Monoclonal and Polyclonal Antibodies," J. Gen. Virol. 71:2909-2914, 1990.
Ni et al., "Comparison of Nucleotide and Deduced Amino Acid Sequence of the 5' Non-Coding Region and Structural Protein Genes of the Wild-Type Japanese Encephalitis Virus Strain SA14 and Its Attenuated Vaccine Derivatives," J. Gen. Virol. 75:1505-1510, 1994.
Ni et al., "Molecular Basis of Attenuation of Neurovirulence of Wild-Type Japanese Encephalitis Virus Strain SA14," J. Gen. Virol. 76:409-413, 1995.
Nitayaphan et al., "Nucleotide Sequence of the Virulent SA-14 Strain of Japanese Encephalitis Virus and Its Attenuated Vaccine Derivative, SA-14-14-2," Virology 177:541-552, 1990.
Pervikov, "Development of Dengue Vaccine," W.H.O. Dengue Bulletin 24, 2000.
Pletnev et al., "Construction and Characterization of Chimeric Tick-Borne Encephalitis/Dengue Type 4 Viruses," Proc. Natl. Acad. Sci. U.S.A. 89:10532-10536, 1992.
Poidinger et al., "Molecular Characterization of the Japanese Encephalitis Serocomplex of the Flavivirus Genus," Virology 218:417-421, 1996.
Rey et al., "The Envelope Glycoprotein From Tick-Borne Encephalitis Virus at 2Å Resolution," Nature 375:291-298, 1995.
Rey, "Dengue Virus Envelope Glycoprotein Structure: New Insight Into Its Interactions During Viral Entry," Proc. Natl. Acad. Sci. U.S.A. 100:6899-6901, 2003.
Rice et al., "Transcription of Infectious Yellow Fever RNA from Full-Length cDNA Templates Produced by In Vitro Ligation," The New Biologist 1:285-296, 1989.
Rothman, "Dengue: Defining Protective Versus Pathologic Immunity," J. Clin. Invest. 113:946-951, 2004.
Ryman et al., "Yellow Fever Virus Envelope Protein has Two Discrete Type-Specific Neutralizing Epitopes," J. Gen. Virol. 78:1353-1356, 1997.
Sabchareon et al., "Protective efficacy of the recombinant, live-attenuated, CYD tetravalent dengue vaccine in Thai schoolchildren: a randomised, controlled phase 2b trial," available on www.thelancet.com Sep. 11, 2012, published in final edited form as: Lancet. 380(9853):1559-67 (2012) (9 pages).
Sabchareon et al., "Safety and Immunogenicity of Tetravalent Live-Attenuated Dengue Vaccines in Thai Adult Volunteers: Role of Serotype Concentration, Ratio, and Multiple Doses," Am. J. Trop. Med. Hyg. 66:264-272, 2002.
Shiu et al., "Genomic Sequence of the Structural Proteins of Louping III Virus: Comparative Analysis with Tick-Borne Encephalitis Virus," Virology 180:411-415, 1991.
Stephenson, "Flavivirus Vaccines," Vaccine 6:471-480, 1988. Abstract only.
Stocks et al., "Signal Peptidase Cleavage at the Flavivirus C-prM Junction: Dependence on the Viral NS2B-3 Protease for Efficient Processing Requires Determinants in C, the Signal Peptide, and prM," J. Virol. 72:2141-2149, 1998.
Sun et al., "Vaccination of Human Volunteers with Monovalent and Tetravalent Live-Attenuated Dengue Vaccine Candidates," Am. J. Trop. Med. Hyg. 69(Suppl 6):24-31, 2003.
Tesh et al., "Efficacy of Killed Virus Vaccine, Live Attenuated Chimeric Virus Vaccine, and Passive Immunization for Prevention of West Nile Virus Encephalitis in Hamster Model," Emerg. Infect. Dis. 8:1392-1397, 2002.
Theiler et al., "The Use of Yellow Fever Virus Modified by In Vitro Cultivation for Human Immunization," Rev. Med. Virol. 10:3-16, 2000.

(56) References Cited

OTHER PUBLICATIONS

Van Der Most et al., "Chimeric Yellow Fever/Dengue Virus as a Candidate Dengue Vaccine: Quantitation of the Dengue Virus-Specific CD8 T-Cell Response," J. Virol. 74:8094-8101, 2000.
Van Epps, "Broadening the Horizons for Yellow Fever: New Uses for an Old Vaccine" J. Exp. Med. 201:165-168, 2005.
Venugopal et al., "Towards a New Generation of Flavivirus Vaccines," Vaccines 12:966-975, 1994.
Vlaycheva et al., "Yellow Fever 17D Virus: Pseudo-Revertant Suppression of Defective Virus Penetration and Spread by Mutations in Domains II and III of the E protein," Virology 327:41-49, 2004.
Volk et al., "Solution Structure and Antibody Binding Studies of the Envelope Protein Domain III from the New York Strain of West Nile Virus," J. Biol. Chem. 279:38755-38761, 2004.
Wang et al., "Comparison of the Genomes of the Wild-Type French Viscerotropic Strain of Yellow Fever Virus with its Vaccine Derivative French Neurotropic Vaccine," J. Gen. Virol. 76:2749-2755, 1995.
Yamshchikov et al., "An Attenuated West Nile Prototype Virus is Highly Immunogenic and Protects Against the Deadly NY99 Strain: A Candidate for Live WN Vaccine Development," Virology, 330:304-312, 2004.
Yang et al., "Induction of Potent Th1-Type Immune Responses from a Novel DNA Vaccine for West Nile Virus New York Isolate (WNV-NY1999)," J. Infect. Dis. 184:809-816, 2001.
International Search Report from WO02/102828 dated Apr. 18, 2003.
International Search Report from WO03/063725 dated Jun. 25, 2003.
International Search Report from WO03/101397 dated Sep. 4, 2003.
International Search Report from WO03/103571 dated Dec. 12, 2003.
International Search Report from WO04/045529 dated Jun. 28, 2004.
International Search Report from WO05/082020 dated Sep. 30, 2005.
International Search Report from WO06/044857 dated May 30, 2006.
International Search Report from WO06/116182 dated Jul. 17, 2006.
European Search Report from European Application No. 05012770, dated Dec. 13, 2005.
Extended European Search Report from European Patent Application No. 10013094.7, dated Jan. 24, 2011.
Substantive prosecution documents from U.S. Appl. No. 10/345,036, filed Jan. 15, 2003 (now U.S. Pat. No. 7,459,160).
Supplementary European Search Report from European Application No. EP 03783570, dated May 10, 2006.
Capeding et al., "Clinical efficacy and safety of a novel tetravalent dengue vaccine in healthy children in Asia: a phase 3, randomised, observer-masked, placebo-controlled trial," Lancet. 384(9951):1358-65 (2014).
Dorigatti, "Refining the characterisation of the Sanofi Pasteur dengue vaccine's efficacy profile using machine learning," 49th Scientific Meeting of the Societa Italiana di Statistica, Jun. 20, 2018. Palermo, Italy. (15 pages).
Hadinegoro et al., "Efficacy and long-term safety of a dengue vaccine in regions of endemic disease," N Engl J Med. 373(13):1195-206 (2015).
Moodie et al., "Neutralizing antibody correlates analysis of tetravalent dengue vaccine efficacy trials in Asia and Latin America," J Infect Dis. 217(5):742-53 (2018).
Rabaa et al., "Genetic epidemiology of dengue viruses in phase III trials of the CYD tetravalent dengue vaccine and implications for efficacy," Elife. 6. pii:e24196 (2017) (22 pages).
Sridhar et al., "Effect of dengue serostatus on dengue vaccine safety and efficacy," N Engl J Med. DOI: 10.1056/NEJMoa1800820 (2018) (14 pages).
Villar et al., "Efficacy of a tetravalent dengue vaccine in children in Latin America," N Engl J Med. 372(2):113-23 (2015).

Fig. 2A. Dose ~0.7 log10 PFU
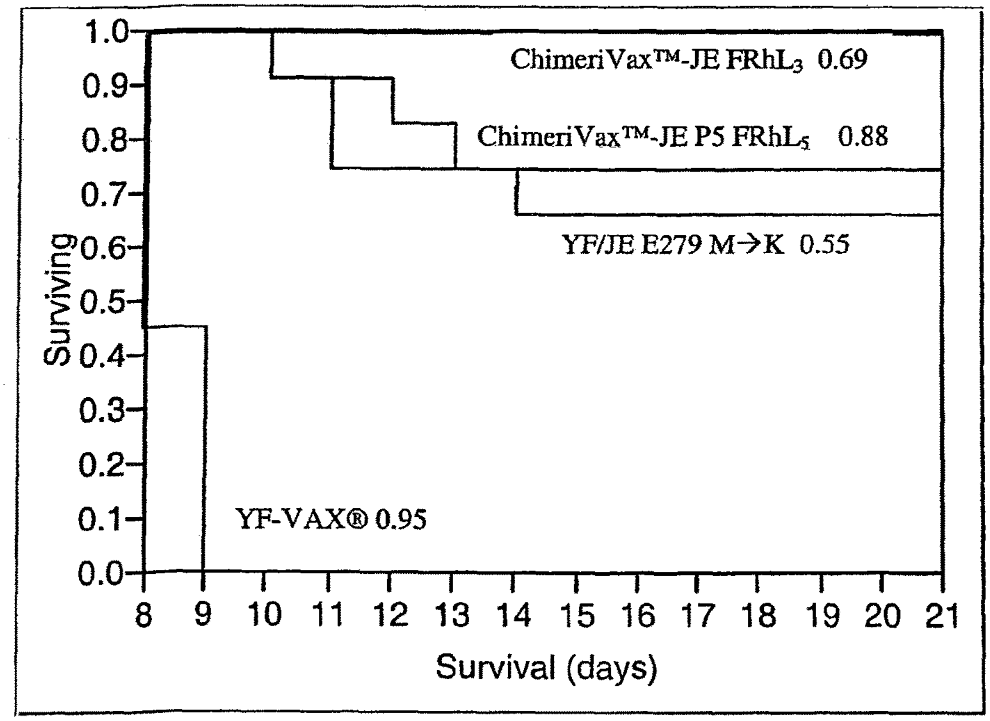
Log rank test $p< 0.0001$, including YF-VAX
Log rank test $p=0.1216$ comparing the three ChimeriVax™-JE constructs Fig. 2B. Dose ~1.7 log10 PFU
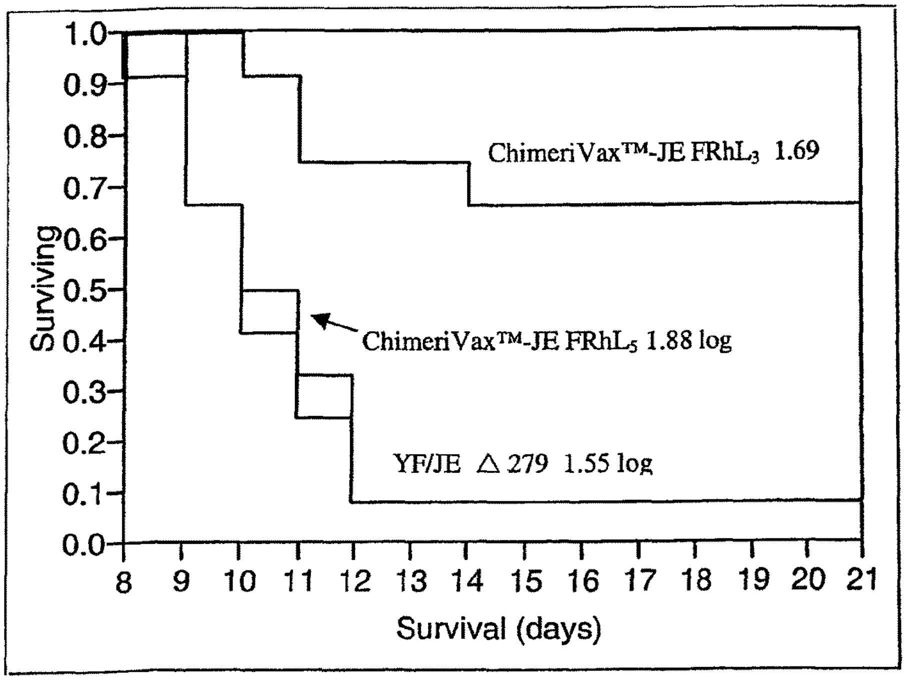
Log rank test p= 0.0016

Fig. 2C. Dose ~2.7 log10 PFU
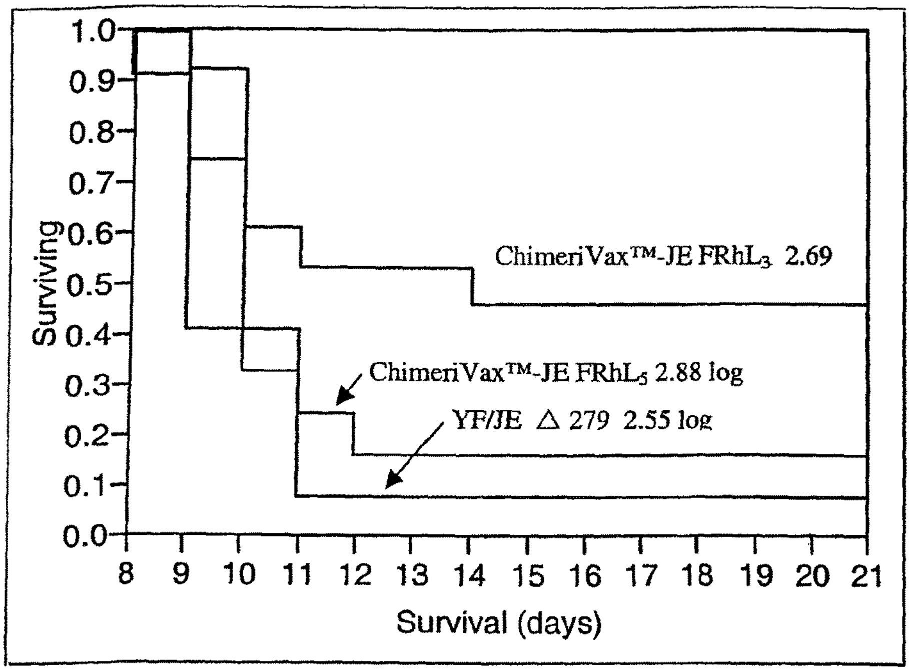
Log rank test p= 0.0558

FLAVIVIRUS VACCINES

This application is a continuation of U.S. Ser. No. 13/668,819, filed Nov. 5, 2012 (U.S. Pat. No. 8,852,914), which is is a continuation of U.S. Ser. No. 13/423,746, filed Mar. 19, 2012 (abandoned), which is a continuation of U.S. Ser. No. 13/198,976, filed Aug. 5, 2011 (abandoned), which is a continuation of U.S. Ser. No. 12/962,216, filed Dec. 7, 2010, (abandoned) which is a continuation of U.S. Ser. No. 12/325,864, filed Dec. 1, 2008 (abandoned), which is a continuation of U.S. Ser. No. 10/345,036, filed Jan. 15, 2003 (U.S. Pat. No. 7,459,160), which claims priority from U.S. Provisional patent application Ser. Nos. 60/348,949, filed Jan. 15, 2002, and 60/385,281, filed May 31, 2002, the contents of each of which are incorporated herein by reference.

FIELD OF THE INVENTION

This invention relates to flavivirus vaccines.

BACKGROUND OF THE INVENTION

Flaviviruses are small, enveloped, positive-strand RNA viruses, several of which pose current or potential threats to global public health. Yellow fever virus, for example, has been the cause of epidemics in certain jungle locations of sub-Saharan Africa, as well as in some parts of South America. Although many yellow fever infections are mild, the disease can also cause severe, life-threatening illness. The disease state has two phases. The initial or acute phase is normally characterized by high fever, chills, headache, backache, muscle aches, loss of appetite, nausea, and vomiting. After three to four days, these symptoms disappear. In some patients, symptoms then reappear, as the disease enters its so-called toxic phase. During this phase, high fever reappears and can lead to shock, bleeding (e.g., bleeding from the mouth, nose, eyes, and/or stomach), kidney failure, and liver failure. Indeed, liver failure causes jaundice, which is yellowing of the skin and the whites of the eyes, and thus gives "yellow fever" its name. About half of the patients who enter the toxic phase die within 10 to 14 days. However, persons that recover from yellow fever have lifelong immunity against reinfection. The number of people infected with yellow fever virus over the last two decades has been increasing, with there now being about 200,000 yellow fever cases, with about 30,000 deaths, each year. The re-emergence of yellow fever virus thus presents a serious public health concern.

Dengue (DEN) virus is another example of a flavivirus. Dengue viruses are transmitted to humans by mosquitoes (mainly by *Aedes aegypti*) and are the cause of a growing public health problem worldwide. Fifty to one hundred million persons are infected by Dengue virus annually, and rates of infection as high as 6% have been observed in some areas (Gubler, "Dengue and Dengue Hemorrhagic Fever," CABI Publ., New York, Chapter 1, pp. 1-22, 1997; Burke et al., Am. J. Trop. Med. Hyg. 38:172-180, 1988). Four serotypes of Dengue virus (dengue types 1-4) circulate in the Caribbean, Asia, and the Americas. The severe, potentially lethal form of DEN infection [dengue hemorrhagic fever/dengue shock syndrome (DHF/DSS)] is an immunopathological disease occurring in individuals who have sustained sequential infections with different DEN serotypes. Over 3.6 million cases of DHF and 58,000 deaths caused by DHF were reported between 1980 and 1995 (Halstead, "Dengue and Dengue Hemorrhagic Fever," CABI Publ., New York, Chapter 2, pp. 23-44, 1997). Because of the pathogenesis of DHF/DSS, it is generally thought that a optimal dengue vaccine may need to immunize against all four serotypes of Dengue virus simultaneously and induce long-lasting immunity. Despite the extensive efforts that have made towards developing an effective Dengue vaccine since World War II, there is currently no approved dengue vaccine available.

Flaviviruses, including yellow fever virus and dengue virus, have two principal biological properties responsible for their induction of disease states in humans and animals. The first of these two properties is neurotropism, which is the propensity of the virus to invade and infect nervous tissue of the host. Neurotropic flavivirus infection can result in inflammation and injury of the brain and spinal cord (i.e., encephalitis), impaired consciousness, paralysis, and convulsions. The second biological property of flaviviruses is viscerotropism, which is the propensity of the virus to invade and infect vital visceral organs, including the liver, kidney, and heart. Viscerotropic flavivirus infection can result in inflammation and injury of the liver (hepatitis), kidney (nephritis), and cardiac muscle (myocarditis), leading to failure or dysfunction of these organs. Neurotropism and viscerotropism appear to be distinct and separate properties of flaviviruses.

Some flaviviruses are primarily neurotropic (such as West Nile virus), others are primarily viscerotropic (e.g., yellow fever virus and dengue virus), and still others exhibit both properties (such as Kyasanur Forest disease virus). However, both neurotropism and viscerotropism are present to some degree in all flaviviruses. Within the host, an interaction between viscerotropism and neurotropism is likely to occur, because infection of viscera occurs before invasion of the central nervous system. Thus, neurotropism depends on the ability of the virus to replicate in extraneural organs (viscera). This extraneural replication produces viremia, which in turn is responsible for invasion of the brain and spinal cord.

One approach to developing vaccines against flaviviruses is to modify their virulence properties, so that the vaccine virus has lost its neurotropism and viscerotropism for humans or animals. In the case of yellow fever virus, two vaccines (yellow fever 17D and the French neurotropic vaccine) have been developed (Monath, "Yellow Fever," In Plotkin and Orenstein, Vaccines, 3$^{rd}$ ed., 1999, Saunders, Philadelphia, pp. 815-879). The yellow fever 17D vaccine was developed by serial passage in chicken embryo tissue, and resulted in a virus with significantly reduced neurotropism and viscerotropism. The French neurotropic vaccine was developed by serial passages in mouse brain tissue, and resulted in loss of viscerotropism, but retained neurotropism. A high incidence of neurological accidents (post-vaccinal encephalitis) was associated with the use of the French vaccine. Approved vaccines are not currently available for many medically important flaviviruses having viscerotropic properties, such as dengue, West Nile, and Omsk hemorrhagic fever viruses, among others.

Fully processed, mature virions of flaviviruses contain three structural proteins, capsid (C), membrane (M), and envelope (E), and seven non-structural proteins. Immature flavivirions found in infected cells contain pre-membrane (prM) protein, which is a precursor to the M protein. The flavivirus proteins are produced by translation of a single, long open reading frame to generate a polyprotein, followed by a complex series of post-translational proteolytic cleavages of the polyprotein, to generate mature viral proteins (Amberg et al., J. Virol. 73:8083-8094, 1999; Rice, "Flaviviridae," In Virology, Fields (ed.), Raven-Lippincott, New York, 1995, Volume I, p. 937). The virus structural proteins are arranged in the polyprotein in the order C-prM-E.

SUMMARY OF THE INVENTION

The invention provides flaviviruses including one or more hinge region mutations that reduce viscerotropism of the flaviviruses. These flaviviruses can be, for example, yellow fever virus (e.g., a yellow fever virus vaccine strain); a viscerotropic flavivirus selected from the group consisting of Dengue virus, West Nile virus, Wesselsbron virus, Kyasanur Forest Disease virus, and Omsk Hemorrhagic fever virus; or a chimeric flavivirus. In one example of a chimeric flavivirus, the chimera includes the capsid and non-structural proteins of a first flavivirus virus (e.g., a yellow fever virus) and the pre-membrane and envelope proteins of a second flavivirus (e.g., a Japanese encephalitis virus or a Dengue virus (e.g., Dengue virus 1, 2, 3, or 4)) including an envelope protein mutation that decreases viscerotropism of the chimeric flavivirus. In the case of Dengue virus, the mutation can be, for example, in the lysine at Dengue envelope amino acid position 202 or 204. This amino acid can be substituted by, for example, arginine.

The invention also provides vaccine compositions that include any of the viruses described herein and a pharmaceutically acceptable carrier or diluent, as well as methods of inducing an immune response to a flavivirus in a patient by administration of such a vaccine composition to the patient. Patients treated using these methods may not have, but be at risk of developing, the flavivirus infection, or may have the flavivirus infection.

Also included in the invention are methods of producing flavivirus vaccines, involving introducing into a flavivirus a mutation that results in decreased viscerotropism. Further, the invention includes methods of identifying flavivirus (e.g., yellow fever virus or chimeric flavivirus) vaccine candidates, involving (i) introducing a mutation into the hinge region of a flavivirus; and (ii) determining whether the flavivirus including the hinge region mutation has decreased viscerotropism, as compared with a flavivirus virus lacking the mutation.

The flaviviruses of the invention are advantageous because, in having decreased viscerotropism, they provide an additional level of safety, as compared to their non-mutated counterparts, when administered to patients. Additional advantages of these viruses are provided by the fact that they can include sequences of yellow fever virus strainYF17D (e.g., sequences encoding capsid and non-structural proteins), which (i) has had its safety established for >60 years, during which over 350 million doses have been administered to humans, (ii) induces a long duration of immunity after a single dose, and (iii) induces immunity rapidly, within a few days of inoculation. In addition, the vaccine viruses of the invention cause an active infection in the treated patients. As the cytokine milieu and innate immune response of immunized individuals are similar to those in natural infection, the antigenic mass expands in the host, properly folded conformational epitopes are processed efficiently, the adaptive immune response is robust, and memory is established. Moreover, in certain chimeras of the invention, the prM and E proteins derived from the target virus contain the critical antigens for protective humoral and cellular immunity.

Other features and advantages of the invention will be apparent from the following detailed description, the drawings, and the claims.

BRIEF DESCRIPTION OF THE DRAWINGS

FIG. 2 is a series of graphs showing survival distributions of YF-VAX® and ChimeriVax™-JE constructs, with and without a mutation at E279 (M→K). Four day-old suckling mice inoculated by the intracerebral route with (FIG. 2A) approximately 0.7 $\log_{10}$ PFU; (FIG. 2B) approximately 1.7 $\log_{10}$ PFU; and (FIG. 2C) ~2.7 $\log_{10}$ PFU.

DETAILED DESCRIPTION

Figure 1:
FIG. 1 shows plaque size variants produced by ChimeriVax™-JE FRhL$_3$ (large plaque, Panel A) and FRhL$_5$ (small plaque, Panel B). Plaques were stained using rabbit anti-JE antiserum followed by anti-rabbit IgG-horseradish peroxidase.

The invention provides flaviviruses (e.g., yellow fever viruses and chimeric flaviviruses) having one or more mutations that result in decreased viscerotropism, methods for making such flaviviruses, and methods for using these flaviviruses to prevent or to treat flavivirus infection. The mutation (or mutations) in the flaviviruses of the invention is present in the hinge region of the envelope protein, which we have shown plays a role in determining viscerotropism. The viruses and methods of the invention are described further, as follows.

One example of a flavivirus that can be used in the invention is yellow fever virus. Mutations can be made in the hinge region of the envelope of a wild-type infectious clone, e.g., the Asibi infectious clone or an infectious clone of another wild-type, virulent yellow fever virus, and the mutants can then be tested in an animal model system (e.g., in hamster and/or monkey model systems) to identify sites affecting viscerotropism. Reduction in viscerotropism is judged by, for example, detection of decreased viremia and/or liver injury in the model system (see below for additional details). One or more mutations found to decrease viscerotropism of the wild-type virus are then introduced into a vaccine strain (e.g., YF17D), and these mutants are tested in an animal model system (e.g., in a hamster and/or a monkey model system) to determine whether the resulting mutants have decreased viscerotropism. Mutants that are found to have decreased viscerotropism can then be used as new vaccine strains that have increased safety, due to decreased levels of viscerotropism.

Additional flaviviruses that can be used in the invention include other mosquito-borne flaviviruses, such as Japanese encephalitis, Dengue (serotypes 1-4), Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus). All of these viruses have some propensity to infect visceral organs. The viscerotropism of these viruses may not cause dysfunction of vital visceral organs, but the replication of virus in these organs can cause viremia and thus contribute to invasion of the central nervous system. Decreasing the viscerotropism of these viruses by mutagenesis can thus reduce their abilities to invade the brain and to cause encephalitis.

In addition to the viruses listed above, as well as other flaviviruses, chimeric flaviviruses that include one or more mutations that decrease viscerotropism are included in the invention. These chimeras can consist of a flavivirus (i.e., a backbone flavivirus) in which a structural protein (or proteins) has been replaced with a corresponding structural protein (or proteins) of a second virus (i.e., a test or a predetermined virus, such as a flavivirus). For example, the chimeras can consist of a backbone flavivirus (e.g., a yellow fever virus) in which the prM and E proteins of the flavivirus have been replaced with the prM and E proteins of the second, test virus (e.g., a dengue virus (1-4), Japanese encephalitis virus, West Nile virus, or another virus, such as any of those mentioned herein)(the E protein of which has a hinge region mutation as described herein). The chimeric viruses can be made from any combination of viruses. Preferably, the virus against which immunity is sought is the source of the inserted structural protein(s).

A specific example of a chimeric virus that can be included in the vaccines of the invention is the yellow fever human vaccine strain, YF17D, in which the prM protein and the E protein have been replaced with the prM protein and the E protein (including a hinge mutation as described herein) of another flavivirus, such as a Dengue virus (serotype 1, 2, 3, or 4), Japanese encephalitis virus, West Nile virus, St. Louis encephalitis virus, Murray Valley encephalitis virus, or any other flavivirus, such as one of those listed above. For example, the following chimeric flaviviruses, which were deposited with the American Type Culture Collection (ATCC) in Manassas, Va., U.S.A. under the terms of the Budapest Treaty and granted a deposit date of Jan. 6, 1998, can be used to make viruses of the invention: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594). Details of making chimeric viruses that can be used in the invention are provided, for example, in International applications PCT/US98/03894 and PCT/US00/32821; and Chambers et al., J. Virol. 73:3095-3101, 1999, each of which is incorporated by reference herein in its entirety.

As is noted above, mutations that are included in the viruses of the present invention decrease viscerotropism. In one example, these mutations are present in the hinge region of the flavivirus envelope protein. The polypeptide chain of the envelope protein folds into three distinct domains: a central domain (domain I), a dimerization domain (domain II), and an immunoglobulin-like module domain (domain III). The hinge region is present between domains I and II and, upon exposure to acidic pH, undergoes a conformational change (hence the designation "hinge") involved in the fusion of viral and endosomal membranes, after virus uptake by receptor-mediated endocytosis. Numerous envelope amino acids are present in the hinge region including, for example, amino acids 48-61, 127-131, and 196-283 of yellow fever virus (Rey et al., Nature 375:291-298, 1995). Any of these amino acids, or closely surrounding amino acids (and corresponding amino acids in other flavivirus envelope proteins), can be mutated according to the invention, and tested for a resulting decrease in viscerotropism. Mutations can be made in the hinge region using standard methods, such as site-directed mutagenesis. One example of the type of mutation present in the viruses of the invention is substitutions, but other types of mutations, such as deletions and insertions, can be used as well. In addition, as is noted above, the mutations can be present singly or in the context of one or more additional mutations.

The viruses (including chimeras) of the present invention can be made using standard methods in the art. For example, an RNA molecule corresponding to the genome of a virus can be introduced into primary cells, chick embryos, or diploid cell lines, from which (or the supernatants of which) progeny virus can then be purified. Another method that can be used to produce the viruses employs heteroploid cells, such as Vero cells (Yasumura et al., Nihon Rinsho 21, 1201-1215, 1963). In this method, a nucleic acid molecule (e.g., an RNA molecule) corresponding to the genome of a virus is introduced into the heteroploid cells, virus is harvested from the medium in which the cells have been cultured, harvested virus is treated with a nuclease (e.g., an endonuclease that degrades both DNA and RNA, such as Benzonase™; U.S. Pat. No. 5,173,418), the nuclease-treated virus is concentrated (e.g., by use of ultrafiltration using a filter having a molecular weight cut-off of, e.g., 500 kDa), and the concentrated virus is formulated for the purposes of vaccination. Details of this method are provided in U.S. Patent Application Ser. No. 60/348,565, filed Jan. 15, 2002, which is incorporated herein by reference.

The viruses of the invention can be administered as primary prophylactic agents in adults or children at risk of infection, or can be used as secondary agents for treating infected patients. For example, in the case of yellow fever/dengue chimeras, the vaccines can be used in adults or children at risk of Dengue infection, or can be used as secondary agents for treating Dengue-infected patients. Examples of patients who can be treated using the dengue-related vaccines and methods of the invention include (i) children in areas in which Dengue is endemic, such as Asia, Latin America, and the Caribbean, (ii) foreign travelers, (iii) military personnel, and (iv) patients in areas of a Dengue epidemic. Moreover, inhabitants of regions into which the disease has been observed to be expanding (e.g., Argentina, Chile, Australia, parts of Africa, southern Europe, the Middle East, and the southern United States), or regions in which it may be observed to expand in the future (e.g., regions infested with *Aedes aegypti*), can be treated according to the invention.

Formulation of the viruses of the invention can be carried out using methods that are standard in the art. Numerous pharmaceutically acceptable solutions for use in vaccine preparation are well known and can readily be adapted for use in the present invention by those of skill in this art. (See, e.g., *Remington's Pharmaceutical Sciences* ($18^{th}$ edition), ed. A. Gennaro, 1990, Mack Publishing Co., Easton, Pa.) In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with the chimeric yellow fever virus.

The vaccines of the invention can be administered using methods that are well known in the art, and appropriate amounts of the vaccines administered can be readily be determined by those of skill in the art. For example, the viruses of the invention can be formulated as sterile aqueous solutions containing between $10^2$ and $10^7$ infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via the mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the viruses can be administered by mucosal routes as well. Further, the vaccines of the invention can be administered in a single dose or, optionally, administration can involve the use of a priming dose followed by a booster dose that is administered, e.g., 2-6 months later, as determined to be appropriate by those of skill in the art.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

In the case of Dengue virus, against which optimal vaccination can involve the induction of immunity against all four of the dengue serotypes, the chimeric viruses of the present invention can be used in the formulation of tetravalent vaccines. Any or all of the chimeras used in such tetravalent formulations can include a mutation that decreases viscerotropism, as is described herein. The chimeras can be mixed to form tetravalent preparations at any point during formulation, or can be administered in series. In the case of a tetravalent vaccine, to reduce the possibility of viral interference and thus to achieve a balanced immune response, the amounts of each of the different chimeras present in the administered vaccines can vary. Briefly, in one example of such a formulation, at least 5 fold less of the Dengue-2 chimera (e.g., 10, 50, 100, 200, or 500 fold less) is used relative to the other chimeras. In this example, the amounts of the Dengue-1, Dengue-3, and Dengue-4 chimeras can be equivalent or can vary. In another example, the amounts of Dengue-4 and/or Dengue 1 virus can be decreased as well. For example, in addition to using less Dengue-2 chimera, at least 5 fold less of the Dengue-4 chimera (e.g., 10, 50, 100, 200, or 500 fold less) can be used relative to the Dengue-1 and Dengue-3 chimeras; at least 5 fold less of the Dengue-1 chimera (e.g., 10, 50, 100, 200, or 500 fold less) can be used relative to the Dengue-3 and Dengue-4 chimeras; or at least 5 fold less of the Dengue-1 and Dengue-4 chimeras can be used relative to the Dengue-3 chimera. It may be particularly desirable, for example, to decrease the amount of Dengue-1 chimera relative to the amounts of Dengue-3 and/or Dengue-4 chimeras when the E204/E202 mutation described herein is not included in the chimera.

Details of the characterization of one example of a mutation included in the invention, which occurs at position 279 of the envelope protein of a yellow fever/Japanese encephalitis chimera, are provided below. Also provided below are details concerning yellow fever/dengue virus chimeras, in which dengue virus envelope proteins include one or more mutations that decrease viscerotropism. In one example of such a mutation, the lysine at position 204 of the envelope protein of Dengue-1, Dengue-2, or Dengue-4, or the lysine at position 202 of the envelope protein of Dengue-3, which is two amino acids shorter than the envelope proteins of the other Dengue serotypes, is substituted or deleted. This lysine can be, for example, substituted with arginine. Other residues near envelope amino acid 204 (202 for Dengue-3) can also be mutated to achieve decreased viscerotropism. For example, any of amino acids 200-208 or combinations of these amino acids can be mutated. Specific examples include the following: position 202 (K) of Dengue-1; position 202 (E) of Dengue-2; position 200 of Dengue-3 (K); and positions 200 (K), 202 (K), and 203(K) of Dengue-4. These residues can be substituted with, for example, arginine.

Experimental Results

I. Yellow Fever/Japanese Encephalitis Chimera Including a Hinge Region Mutation Summary A chimeric yellow fever (YF)-Japanese encephalitis (JE) vaccine (ChimeriVax™-JE) was constructed by insertion of the prM-E genes from the attenuated JE SA14-14-2 vaccine strain into a full-length cDNA clone of YF 17D virus. Passage in fetal rhesus lung (FRhL) cells led to the emergence of a small-plaque virus containing a single Met→Lys amino acid mutation at E279, reverting this residue from the SA14-14-2 to the wild-type amino acid. A similar virus was also constructed by site-directed mutagenesis. The E279 mutation is located in a beta-sheet in the hinge region of the E protein, which is responsible for a pH-dependent conformational change during virus penetration from the endosome into the cytoplasm of an infected cell. In independent transfection-passage studies in FRhL or Vero cells, mutations appeared most frequently in hinge 4 (bounded by amino acids E266 to E284), reflecting genomic instability in this functionally important region. The E279 reversion caused a significant increase in neurovirulence, as determined by LD50 and survival distribution in suckling mice and by histopathology in rhesus monkeys. Based on sensitivity and comparability of results with monkeys, the suckling mouse is an appropriate host for safety testing of flavivirus vaccine candidates for neurotropism. The E279 Lys virus was restricted with respect to extraneural replication in monkeys, as viremia and antibody levels (markers of viscerotropism) were significantly reduced as compared to E279 Met virus.

Background

The study of chimeric viruses has afforded new insights into the molecular basis of virulence and new prospects for vaccine development. For example, molecular clones of positive-strand alphaviruses (Morris-Downes et al., Vaccine 19:3877-3884, 2001; Xiong et al., Science 243:1188-1191, 1991) and flaviviruses (Bray et al., Proc. Natl. Acad. Sci. U.S.A. 88:10342-10346, 1991; Chambers et al., J. Virol. 73:3095-3101, 1999; Guirakhoo et al., J. Virol. 75:7290-7304, 2001; Huang et al., J. Virol. 74:3020-3028, 2000) have been modified by insertion of structural genes encoding the viral envelope and determinants involved in neutralization, cell attachment, fusion, and internalization. The replication of these chimeric viruses is controlled by nonstructural proteins and the non-coding termini expressed by the parental strain, while the structural proteins from the donor genes afford specific immunity. The biological characteristics of chimeric viruses are determined by both the donor and recipient virus genes. By comparing constructs with nucleotide sequence differences across the donor genes, it is possible to dissect out the functional roles of individual amino acid residues in virulence and attenuation.

Using a chimeric yellow fever (YF) virus that incorporated the prM-E genes from an attenuated strain (SA14-14-2) of Japanese encephalitis (JE), a detailed examination was made of the role of 10 amino acid mutations that distinguished the attenuated JE virus from virulent, wild-type JE Nakayama virus (Arroyo et al., J. Virol. 75:934-942, 2001). The virulence factors were defined by reverting each mutation singly or as clusters to the wild-type sequence and determining the effects on neurovirulence for young adult mice inoculated by the intracerebral (IC) route with $10^4$ plaque-forming units (PFU). All of the single-site revertant viruses remained highly attenuated, and reversions at 3 or 4 residues were required to restore a neurovirulent phenotype. Only one single-site revertant (E279 Met→Lys) showed any evidence of a change in virulence, with 1 of 8 animals succumbing after IC inoculation.

In order to explore further the functional role of the E279 determinant, we compared chimeric YF/JE viruses that differed at this amino acid residue for their abilities to cause encephalitis in suckling mice and monkeys. IC inoculation of monkeys is routinely used as a test for safety of flavivirus and other live vaccines, and quantitative pathological examination of brain and spinal cord tissue provides a sensitive method for distinguishing strains of the same virus with subtle differences in neurovirulence (Levenbook et al., J. Biol. Stand. 15: 305-313, 1987). Suckling mice provide a more sensitive model than older animals, since susceptibility to neurotropic flaviviruses is age-dependent (Monath et al., J. Virol. 74:1742-1751, 2000). The results confirmed that the single Met→Lys amino acid mutation at E279 conferred an increase in neurovirulence. This mutation is located in the 'hinge' region of the E protein, which is responsible for a pH-dependent conformational change during virus penetration from the endosome into the cytoplasm of an infected cell (Reed et al., Am. J. Hyg. 27:493-497, 1938). Importantly, the suckling mouse was shown to predict the virulence profile in rhesus monkeys. Based on the detection of a change in neurovirulence conferred by a point mutation, we propose that the suckling mouse is an appropriate host for safety testing of flavivirus vaccine candidates for neurotropism.

While enhancing neurovirulence, the E279 mutation appeared to have the opposite effect on viscerotropism, as measured by decreased viremia and antibody response in monkeys, accepted markers of this viral trait (Wang et al., J. Gen. Virol. 76:2749-2755, 1995).

Materials and Methods

Viruses

Development of the ChimeriVax™-JE vaccine began by cloning a cDNA copy of the entire 11-kilobase genome of YF 17D virus (Chambers et al., J. Virol. 73:3095-3101, 1999). To accomplish this, YF 17D genomic sequences were propagated in two plasmids, which encode the YF sequences from nucleotide (nt) 1-2276 and 8279-10,861 (plasmid YF5'3'IV), and from 1373-8704 (plasmid YFM5.2), respectively. Full-length cDNA templates were generated by ligation of appropriate restriction fragments derived from these plasmids. YF sequences within the YF 5'31V and YFM5.2 plasmids were replaced by the corresponding JE (SA14-14-2) pr-ME sequences, resulting in the generation of YF5'3'IV/JE (prM-E') and YFM5.2/JE (E'-E) plasmids. These plasmids were digested sequentially with restriction endonucleases NheI and BspEI. Appropriate fragments were ligated with T4 DNA ligase, cDNA was digested with XhoI enzyme to allow transcription, and RNA was produced from an Sp6 promoter. Transfection of diploid fetal rhesus lung (FRhL) cells with full-length RNA was performed by electroporation. Supernatant containing virus was harvested when cytopathic effect was observed (generally day 3), clarified by low-speed centrifugation and sterile-filtered at 0.22 μm. Fetal bovine serum (FBS) 50% v/v final concentration was added as a stabilizer. The virus was titrated by plaque assay in Vero cells, as previously described (Monath et al., Vaccine 17:1869-1882, 1999). The chimeric virus was sequentially passed in FRhL or Vero cells (Vero-PM, Aventis Pasteur, Marcy l'Étoile, France) at a multiplicity of infection of approximately 0.001. Commercial yellow fever 17D vaccine (YF-VAX®) was obtained from Aventis-Pasteur (formerly Pasteur-Mérieux-Connaught), Swiftwater, Pa.

Site-directed Mutagenesis

Virus containing a single-site Met→Lys reversion at residue E279 was generated by oligo-directed mutagenesis as described (Arroyo et al., J. Virol. 75:934-942, 2001). Briefly, a plasmid (pBS/JE SA14-14-2) containing the JE SA-14-14-2 E gene region from nucleotides 1108 to 2472 (Cecilia et al., Virology 181:70-77, 1991) was used as template for site-directed mutagenesis. Mutagenesis was performed using the Transformer site-directed mutagenesis kit (Clontech, Palo Alto, Calif.) and oligonucleotide primers synthesized at Life Technologies (Grand Island, N.Y.). Plasmids were sequenced across the E region to verify that the only change was the engineered mutation. A region encompassing the E279 mutation was then subcloned from the pBS/JE plasmid into pYFM5.2/JE SA14-14-2 (Cecilia et al., Virology 181:70-77, 1991) using the NheI and EheI (KasI) restriction sites. Assembly of full-length DNA and SP6 transcription were performed as described above; however, RNA transfection of Vero cells was performed using Lipofectin (Gibco/BRL).

Sequencing

RNA was isolated from infected monolayers by Trizol® (Life Technologies). Reverse transcription was performed with Superscript II Reverse Transcriptase (RT) and a long-RT protocol (Life Technologies), followed by RNaseH treatment (Promega) and long-PCR (XL PCR, Perkin-Elmer/ABI). RT, PCR, and sequencing primers were designed using YF17D strain sequence (GeneBank Accession number K02749) and JE-SA14-14-2 strain sequence (GeneBank Accession number D90195) as references. PCR products were gel-purified (Qiaquick gel-extraction kit from Qiagen) and sequenced using Dye-Terminator dRhodamine sequencing reaction mix (Perkin-Elmer/ABI). Sequencing reactions were analyzed on a model 310 Genetic Analyzer (Perkin-Elmer/ABI) and DNA sequences were evaluated using Sequencher 3.0 (GeneCodes) software.

Plaque Assays and Neutralization Tests

Plaque assays were performed in 6 well plates of monolayer cultures of Vero cells. After adsorption of virus for 1 hour incubation at 37° C., the cells were overlaid with agarose in nutrient medium. On day 4, a second overlay was added containing 3% neutral red. Serum-dilution, plaque-reduction neutralization tests were performed as previously described (Monath et al., Vaccine 17:1869-1882, 1999).

Weaned Mouse Model

Groups of 8 to 10 female 4 week old ICR mice (Taconic Farms, Inc. Germantown, N.Y.) were inoculated IC with 30 μL of chimeric YF/JE SA14-14-2 (ChimeriVax™-JE) constructs with (dose 4.0 $\log_{10}$ PFU in) or without (3.1 $\log_{10}$ PFU) the E279 mutation. An equal number of mice were inoculated with YF-VAX® or diluent. Mice were followed for illness and death for 21 days.

Suckling Mouse Model

Pregnant female ICR mice (Taconic Farms) were observed through parturition in order to obtain litters of suckling mice of exact age. Suckling mice from multiple litters born within a 48 hour interval were pooled and randomly redistributed to mothers in groups of up to 121 mice. Litters were inoculated IC with 20 μL of serial tenfold dilutions of virus and followed for signs of illness and death for 21 days. The virus inocula were back-titrated. 50% lethal dose ($LD_{50}$) values were calculated by the method of Reed and Muench (Morris-Downes et al., Vaccine 19:3877-3884, 2001). Univariate survival distributions were plotted and compared by log rank test.

Monkey Model

The monkey neurovirulence test was performed as described by Levenbook et al. (Levenbook et al., J. Biol. Stand. 15: 305-313, 1987) and proscribed by WHO regulations for safety testing YF 17D seed viruses (Wang et al., J. Gen. Virol. 76:2749-2755, 1995). This test has previously been applied to the evaluation of ChimeriVax™-JE vaccines, and results of tests on $FRhL_3$ virus were described (Monath et al., Curr. Drugs—Infect. Dis., 1:37-50; 2001; Monath et al., Vaccine 17:1869-1882, 1999). Tests were performed at Sierra Biomedical Inc. (Sparks, Nev.), according to the U.S. Food and Drug Administration Good Laboratory Practice (GLP) regulations (21 C.F.R., Part 58). On Day 1, ten (5 male, 5 female) rhesus monkeys weighing 3.0-6.5 kg received a single inoculation of 0.25 mL undiluted ChimeriVax™-JE virus with or without the E279 Met→Lys mutation or YF-VAX® into the frontal lobe of the brain. Monkeys were evaluated daily for clinical signs and scored as 0 (no signs), 1 (rough coat, not eating), 2 (high-pitched voice, inactive, slow moving, 3 (shaky movements, tremors, incoordination, limb weakness), and 4 (inability to stand, limb paralysis, death). The clinical score for each monkey is the mean of the animal's daily scores, and the clinical score for the treatment group is the arithmetic mean of the individual clinical scores. Viremia levels were measured by plaque assay in Vero cells using sera collected on days 2-10. On day 31, animals were euthanized, perfused with isotonic saline-5% acetic acid followed by neutral-buffered 10% formalin, and necropsies were performed. Brains and spinal cords were fixed, sectioned and stained with gallocyanin. Neurovirulence was assessed by the presence and severity of lesions in various anatomical formations of the central nervous system. Severity was scored within each tissue block using the scale specified by WHO (Wang et al., J. Gen. Virol. 76:2749-2755, 1995):

Grade 1: Minimal: 1-3 small focal inflammatory infiltrates. A few neurons may be changed or lost.

Grade 2: Moderate: more extensive focal inflammatory infiltrates. Neuronal changes or loss affects not more than one-third of neurons.

Grade 3: Severe: neuronal changes or loss affecting 33-90% of neurons; moderate focal or diffuse inflammatory changes Grade 4: Overwhelming; more than 90% of neurons are changed or lost, with variable but frequently severe inflammatory infiltration Structures involved in the pathologic process most often and with greatest severity were designated 'target areas,' while those structures discriminating between wild-type JE virus and ChimeriVax™-JE were designated 'discriminator areas.' The substantia nigra constituted the 'target area' and the caudate nucleus, globus pallidus, putamen, anterior/medial thalamic nucleus, lateral thalamic nucleus, and spinal cord (cervical and lumbar enlargements) constituted 'discriminator areas' (Monath et al., Curr. Drugs Infect. Dis., 1:37-50, 2001), as previously shown for YF 17D (Levenbook et al., J. Biol. Stand. 15:305-313, 1987). All neuropathological evaluations were done by a single, experienced investigator who was blinded to the treatment code. Separate scores for target area, discriminator areas, and target+discriminator areas were determined for each monkey, and test groups compared with respect to average scores. Other areas of the brainstem (nuclei of the midbrain in addition to substantia nigra; pons; medulla; and cerebellum) and the leptomeninges were also examined. Statistical comparisons of mean neuropathological scores (for the target area, discriminator areas, and target+discriminator areas) were performed by Student's t test, 2-tailed. In addition to neuropathological examination, the liver, spleen, adrenal glands, heart, and kidneys were examined for pathologic changes by light microscopy.

Genome Stability

To ascertain the genetic stability of the YF/JE chimeric virus, and to search for 'hot spots' in the vaccine genome that are susceptible to mutation, multiple experiments were performed in which RNA was used to transfect cells and the progeny virus serially passaged in vitro, with partial or complete genomic sequencing performed at low and high passage levels. Passage series were performed starting with the transfection step in FRhL or Vero-PM cells. Serial passage of the virus was performed at low MOI in cell cultures grown in T25 or T75 flasks. At selected passage levels, duplicate samples of viral genomic RNA were extracted, reverse-transcribed, amplified by PCR, and the prM-E region or full genomic sequence determined.

Results

Generation of Single-site Mutant Viruses by Empirical Passage

The chimeric YF/JESA14-14-2 (ChimeriVax™-JE) virus recovered from transfected FRhL cells ($FRhL_1$) was passed sequentially in fluid cultures of these cells at an MOI of approximately 0.001. As is described below, at passage 4 we noted a change in plaque morphology, which was subsequently shown to be associated with a T→G transversion at nucleotide 1818 resulting in an amino acid change (Met→Lys) at position 279 of the E protein.

Plaques were characterized at each passage level and classified into 3 categories based on their sizes measured on day 6 (large, L~>1.0 mm, medium, M~0.5-1 mm, and small, S~<0.5 mm). The plaque size distribution was determined by counting 100 plaques. $FRhL_3$ ($3^{rd}$ ) passage) virus contained 80-94% L and 6-20% S plaques. At $FRhL_5$ ($5^{th}$ passage), a change in plaque size was detected, with the emergence of S plaques comprising >85% of the total plaque population (FIG. 1). The $FRhL_4$ virus was intermediate, with 40% large and 60% small plaques. Full genomic sequencing of the $FRhL_5$ virus demonstrated a single mutation at E279. The full genome consensus sequence of the $FRhL_5$ chimera, with careful inspection for codon heterogeneity, confirmed that this was the only detectable mutation present in the virus. The full genome consensus sequence of the $FRhL_3$ virus revealed no detectable mutations compared to the parental YF/JESA14-14-2 chimeric virus (Arroyo et al., J. Virol. 75:934-942, 2001) (Table 1).

Ten large, medium, and small plaques were picked from $FRhL_3$, $_{-4}$ and $_{-5}$, and amplified by passage in fluid cultures of FRhL cells. After amplification, the supernatant fluid was plagued on Vero cells. Attempts to isolate the S plaque phenotype from $FRhL_3$ failed and all isolated L or S size plaques produced a majority of L plaques after one round of amplification in FRhL cells. At the next passage ($FRhL_4$), where 60% of plaques were of small size, it was possible to isolate these plaques by amplification in FRhL cells. At $FRhL_5$, the majority of plaques (85-99%) were of small size, and amplification of both L and S individual plaques resulted in majority of S size. Sequencing the prM-E genes of the S and L plaque phenotypes from $FRhL_3$ revealed identical sequences to the parent SA14-14-2 genes used for construction of ChimeriVax™-JE, whereas S plaques isolated from either $FRhL_4$ or $FRhL_5$ virus revealed the mutation (Met→Lys) at E279.

Animal Protocols

All studies involving mice and nonhuman primates were conducted in accordance with the USDA Animal Welfare Act (9 C.F.R., Parts 1-3) as described in the Guide for Care and Use of Laboratory Animals.

Virulence for Weaned Mice

Ten female ICR mice 4 weeks of age were inoculated IC with approximately 3.0 $\log_{10}$ PFU of $FRhL_3$, $_{-4}$, or $_{-5}$ virus in separate experiments; in each study 10 mice received an equivalent dose (approximately 3.3 $\log_{10}$ PFU) of commercial yellow fever vaccine (YF-VAX®, Aventis Pasteur, Swiftwater Pa.). None of the mice inoculated with chimeric viruses showed signs of illness or died, whereas 70-100% of control mice inoculated with YF-VAX® developed paralysis or died. In another experiment, 8 mice were inoculated IC with $FRhL_5$ (3.1 $\log_{10}$ PFU) or the YF/JE single-site E279 revertant (4.0 $\log_{10}$ PFU) and 9 mice received YF-VAX® (2.3 $\log_{10}$ PFU). None of the mice inoculated with the chimeric constructs became ill, whereas 6/9 (67%) of mice inoculated with YF-VAX® died.

Virulence for Suckling Mice

Two separate experiments were performed in which YF/JESA14-14-2 chimeric viruses with and without the E279 mutation were inoculated IC at graded doses into suckling mice (Table 2). YF-VAX® was used as the reference control in these experiments. $LD_{50}$ and average survival times (AST) were determined for each virus.

In the first experiment using mice 8.6 days old, $FRhL_5$ virus containing the single site reversion (Met→Lys) at E279 was neurovirulent, with a $\log_{10}$ $LD_{50}$ of 1.64 whereas the $FRhL_3$ virus lacking this mutation was nearly a virulent, with only 1 of 10 mice dying in the highest dose groups (Table 2). At the highest dose (approximately 3 $\log_{10}$ PFU), the AST of the $FRhL_5$ virus was shorter (10.3 days) than that of the $FRhL_3$ virus (15 days).

A second experiment was subsequently performed to verify statistically that a single site mutation in the E gene is detectable by neurovirulence test in suckling mice. In this experiment outbred mice 4 days of age were inoculated IC with graded doses of ChimeriVax™-JE $FRhL_3$ (no mutation), ChimeriVax™-JE $FRhL_5$ (E279 Met→Lys), or a YF/JE chimera in which a single mutation E279 (Met→Lys) was introduced at by site-directed mutagenesis (Arroyo et al., J. Virol. 75:934-942, 2001). The $LD_{50}$ values of the two viruses containing the E279 mutation were >10-fold lower than the $FRhL_3$ construct without the mutation (Table 2) indicating that the E279 Met→Lys mutation increased the neurovirulence of the chimeric virus. There were statistically significant differences between the viruses in the survival distributions (FIG. 2). At the lowest dose (~0.7 $\log_{10}$ PFU), the YF/JE chimeric viruses were significantly less virulent than YF-VAX® (log rank p<0.0001). The viruses with the E279 Met→Lys mutation had similar survival curves that differed from the FRhL3 virus no mutation), but the difference did not reach statistical significance (log rank p=0.1216). However, at higher doses (~1.7 and ~2.7 $\log_{10}$ PFU), the survival distributions of the E279 mutant viruses were significantly different from $FRhL_3$ virus.

Figure 3:
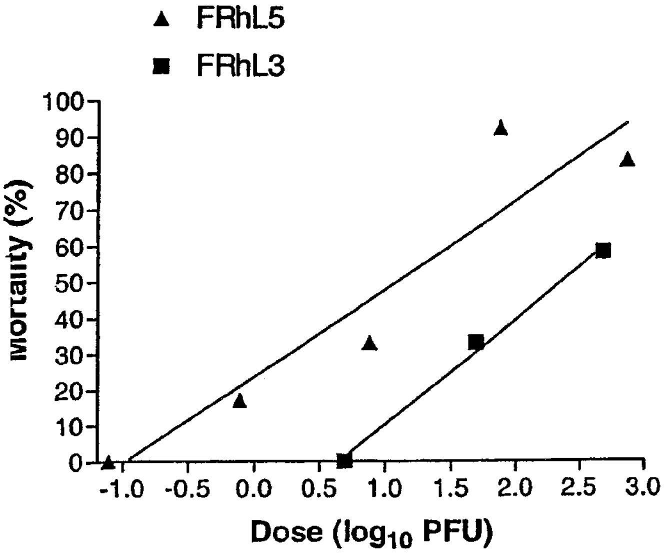
FIG. 3 is a graph of regression analysis, mortality vs. virus dose, showing similar slopes and parallel lines for viruses with (FRhL$_5$) and without (FRhL$_3$) the Met to Lys reversion, allowing statistical comparison. The FRhL$_5$ virus was 18.52 times more potent (virulent) than FRhL$_3$ ($p<0.0001$).

Analysis of mortality ratio by virus dose revealed similar slopes and parallel regression lines (FIG. 3). The $FRhL_5$ virus was 18.52 times more potent (virulent) than $FRhL_3$ (95% fiducial limits 3.65 and 124.44, p<0.0001).

Monkey Neurovirulence Test

None of the 20 monkeys inoculated with ChimeriVax™-JE $FRhL_3$ or $FRhL_5$ viruses developed signs of encephalitis, whereas 4/10 monkeys inoculated with YF-VAX® developed grade 3 signs (tremors) between days 15-29, which resolved within 6 days of onset. Mean and maximum mean clinical scores were significantly higher in the YF-VAX® group than in the two ChimeriVax™-JE groups. There was no difference in clinical score between groups receiving ChimeriVax™-JE viruses with and without the E279 mutation (Table 3).

There were no differences in weight changes during the experiment between treatment groups. Pathological examination revealed no alterations of liver, spleen, kidney, heart, or adrenal glands attributable to the viruses, and no differences between treatment groups.

Histopathologic examination of the brain and spinal cord revealed significantly higher lesion scores for monkeys inoculated with YF-VAX® than for ChimeriVax™-JE virus $FRhL_3$ and $FRhL_5$ (Table 3). The combined target+discriminator scores (±SD) for YF-VAX® was 1.17 (±0.47). The scores for the ChimeriVax™-JE $FRhL_3$ (E279 Met) and $FRhL_5$ (E279 Lys) were 0.29 (±0.20), (p=0.00014 vs. YF-VAX®) and 0.54 (±0.28), (p=0.00248 vs. YF-VAX®), respectively.

The discriminator area score and combined target+discriminator area score for ChimeriVax™-JE $FRhL_5$ containing the Met→Lys reversion at E279 were significantly higher than the corresponding scores for ChimeriVax™-JE $FRhL_3$ (Table 3).

The main symptom in monkeys inoculated with YF-VAX® was tremor, which may reflect lesions of the cerebellum, thalamic nuclei, or globus pallidus. No clear histological lesions were found in the cerebellar cortex, *N. dentatus*, or other cerebellar nuclei, whereas inflammatory lesions were present in the thalamic nuclei and globus pallidus in all positive monkeys.

Interestingly, there was an inverse relationship between neurovirulence and viscerotropism of the E279 revertant, as reflected by viremia. The WHO monkey neurovirulence test includes quantitation of viremia as a measure of viscerotropism (World Health Organization, "Requirements for yellow fever vaccine," Requirements for Biological Substances No. 3, revised 1995, WHO Tech. Rep. Ser. 872, Annex 2, Geneva: WHO, 31-68, 1998). This is rational, based on observations that intracerebral inoculation results in immediate seeding of extraneural tissues (Theiler, "The Virus," In Strode (ed.), Yellow Fever, McGraw Hill, New York, N.Y., 46-136, 1951). Nine (90%) of 10 monkeys inoculated with YF-VAX® and 8 (80%) of 10 monkeys inoculated with ChimeriVax™-JE $FRhL_3$ became viremic after IC inoculation. The level of viremia tended to be higher in the YF-VAX® group than in the ChimeriVax™-JE $FRhL_3$ group, reaching significance on Day 4. In contrast, only 2 (20%) of the animals given $FRhL_5$ virus (E279 Met→Lys) had detectable, low-level viremias (Table 4), and the mean viremia was significantly lower than $FRhL_3$ virus on days 3 and 4 (and nearly significant on day 5). Thus, the $FRhL_5$ revertant virus displayed increased neurovirulence, but decreased viscerotropism compared to $FRhL_3$ virus. Sera from monkeys inoculated with ChimeriVax™-JE $FRhL_3$ and $FRhL_5$ were examined for the presence of plaque size variants. Only L plaques were observed in sera from monkeys inoculated with the $FRhL_3$, whereas the virus in blood of monkeys inoculated with $FRhL_5$ had the appropriate S plaque morphology.

Immunogenicity

All monkeys in all three groups developed homologous neutralizing antibodies 31 days post-inoculation to yellow fever (YF-VAX® group) or ChimeriVax™-JE (ChimeriVax™ groups), with the exception of 1 animal ($FRhL_5$, RAK22F), which was not tested due to sample loss. However, the geometric mean antibody titer (GMT) was significantly higher in the monkeys inoculated with $FRhL_3$ (GMT 501) than with $FRhL_5$ (GMT 169, p=0.0386, t-test).

Genome Stability

Figure 4:
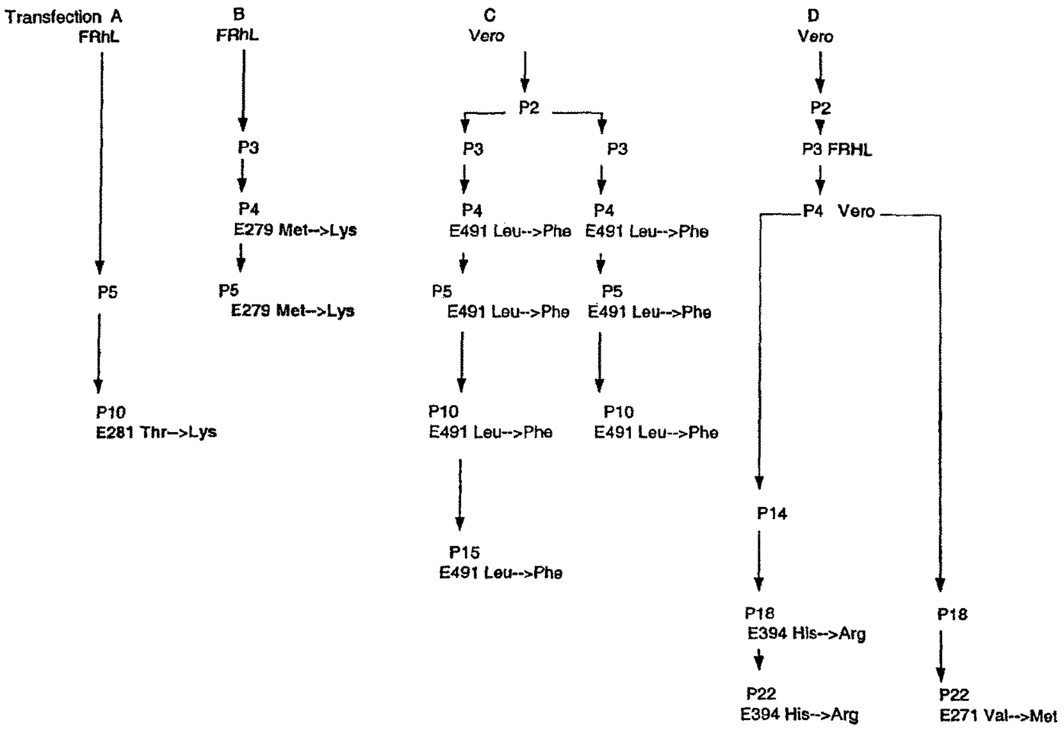
FIG. 4 shows the results of independent RNA transfection and passage series of ChimeriVax™-JE virus in FRhL and Vero cells. The emergence of mutations in the prME genes by passage level is shown.
Figure 5:
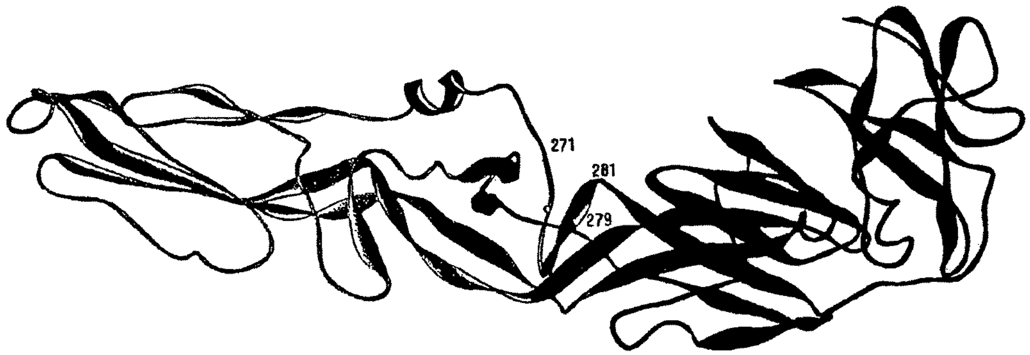
FIG. 5 is a three-dimensional model of the flavivirus envelope glycoprotein ectodomain showing locations of mutations in the hinge region occurring with adaptation in FRhL or Vero cells. The sequence of the JE envelope glycoprotein (strain JaOArS982; Sumiyoshi et al., Virology 161:497-510, 1987) was aligned to one of the TBE structural templates (Rey et al., Nature 375:291-298, 1995) as an input for automated homology modeling building by the method of SegMod (Segment Match Modeling) using LOOK software (Molecular Application Group, Palo Alto, Calif.).

Two separate transfections of ChimeriVax™-JE RNA were performed in each of two cell strains, FRhL and Vero, and progeny viruses were passed as is shown in FIG. 4. The FRhL passage series B resulted in appearance of the E279 reversion at $FRhL_4$ as described above. Interestingly, a separate passage series (A) in FRhL cells also resulted in the appearance of a mutation (Thr→Lys) in an adjacent residue at E281, and one of the passage series in Vero cells resulted in a Val→Lys mutation at E271. Other mutations selected in Vero cells were in domain III or within the transmembrane domain. All viruses containing mutations shown in FIG. 2 were evaluated in the adult mouse neurovirulence test and were found to be avirulent.

II. Yellow Fever/Dengue Chimera Including Hinge Region Mutation

Summary

ChimeriVax™-DEN1 virus was produced using the prME genes of a wild type strain of dengue 1 virus [(Puo359) isolated in 1980 in Thailand] inserted into the yellow fever virus (strain 17D) backbone (Guirakhoo et al., J. Virol. 75:7290-7304, 2001). During production of a Pre-Master Seed virus for ChimeriVax™-DEN1 in Vero cells, a clone (clone E) containing a single nucleotide change from A to G at position 1590, which resulted in an amino acid substitution from K to R at position 204 on the envelope protein E, was isolated and plaque purified. The virus exhibited attenuation for 4-day-old suckling mice and produced a lower viremia (viscerotropism) than its parent (non-mutant) virus when inoculated by subcutaneous route into monkeys. Another clone (clone J-2) without mutation was selected, plaque purified, and used to produce a PMS virus stock at passage 7 (P7). This virus did not undergo any mutations when passaged under laboratory conditions up to P10 in Vero cells. However, upon one passage under cGMP conditions to produce a Master Seed virus (P8) from PMS stock, the same mutation at position 1590 (A to G) emerged. Similar to clone E, the P8 virus produced larger plaques than P7 virus and was attenuated for suckling mice. The E204 position, which is conserved in all dengue viruses, can thus be manipulated in ChimeriVax™-DEN (serotypes 1-4) viruses to achieve a balance between attenuation and immunogenicity of the vaccine candidates for humans.

Results and Discussion

Production of Pre-Master Seeds for ChimeriVax-DEN1 Viruses

Production of plaque purified Pre-Master Seed (PMS) viruses for DEN1 was carried out as follows. Plaque purification was started with the virus at Passage 2 (P2) post RNA transfection. Two PMS viruses (uncloned at P2 and cloned at P7) were produced in Aventis Vero LS10 cells at passage 142 using a qualified cell bank obtained from Aventis at passage 140. Cloned viruses were obtained after 3 rounds of plaque purification and sequenced across the full genome to assure lack of mutations. Generally, if a clone contained an amino acid substitution, it was not used as a PMS virus candidate. Other clones were prepared and sequenced until a clone without mutation was identified, which was then subjected to plaque purification and sequencing.

Sequencing

For sequencing, viral RNA was extracted from each individual virus sample (generally 0.25 ml) using TRI-Reagent LS (Molecular Research Center) or Trizol LS (a similar reagent from Gibco) and dissolved in 0.20 ml of RNase-free water. The extracted RNA was then used as a template for RT-PCR. The entire genome was amplified in five overlapping amplicons of ~2-3 kb in length (fragments I through V) with the Titan One-Tube RT-PCR kit (Roche). The RT-PCR fragments were purified using QIAquick PCR Purification kit (Qiagen) or agarose gel-purified using QIAquick Gel Extraction kit (Qiagen). Sequencing reactions were done using CEQ Dye Terminator Cycle Sequencing kit (Beckman) and a collection of YF-specific oligonucleotide primers of both positive and negative orientation to read both strands of the amplicons. Sequencing reaction products were purified using DyeEx Spin kit (Qiagen), and resolved with a CEQ2000 automated sequencer (Beckman Coulter). Generated sequencing data were aligned and analyzed with Sequencher 3.0 (GeneCodes) software. Nucleotide heterogeneities were registered only when a heterogeneous signal was observed in all chromatograms representing both plus- and minus-strand sequencing reactions.

As is shown in Table 5, the uncloned P2 virus did not have any mutations, but acquired 5 amino acid mutations (heterogeneity) within the envelope protein E by P5. Interestingly, the only mutation that was stable (further selected) at P15 was the 204 mutation. A repeat passage experiment starting from uncloned P2 virus (up to P15) revealed the same mutation (K to R) at E204 position being selected in Vero cells.

Different clones of ChimeriVax-DEN1 (A-J) were selected by direct plaque to plaque purification and sequenced at various stages to identify mutations. The most frequent mutation was the E251 (V>F) substitution, which occurred in clones A, B, D, and G followed by E204 (K>R), which was found in clones E and F, as well as in uncloned viruses. The mutation at E311 (E>D) was only found in clones C and D. Interestingly, clone J was free from mutations up to P10. However, when a Master Seed (MS) of this virus was produced from P7 (PMS) under cGMP manufacturing, the same substitution at E204 reemerged (only after 1 passage). This mutation was stable when P20 virus was sequenced (Table 5). Clones containing the E204 mutation produced larger plaques (~2 mm in diameter) than non-mutant viruses (~1 mm in diameter) (Table 9). The original construct of this virus at Vero P4 (previously shown to produce a low level of viremia in monkeys) also contained the same E204 mutation (Guirakhoo et al., J. Virol. 75:7290-7304, 2001). The role of this mutation in the biology of the virus could not be understood previously because: a) the original construct contained an additional mutation (nucleotide A to G causing an amino acid change from H to R) at M39 besides the E204 mutation; b) the neurovirulence of the original construct was evaluated only in 3-4 week old mice, which are not sensitive enough to reveal attenuation of ChimeriVax-DEN1 virus or any other ChimeriVax™-DEN viruses (Guirakhoo et al., J. Virol. 75:7290-7304, 2001); and c) there was no ChimeriVax™-DEN1 virus (without mutation) available for comparison to determine changes in neurovirulence or viscerotropism phenotype of the virus.

Since chimeric viruses are attenuated for 3-4 week old mice, we developed a more sensitive test (using suckling mice of 4-8 days old) to test subtle differences in neurovirulence of different clones.

Mouse Neurovirulence

The mouse neurovirulence test, using 3-4 week old mice, is performed as a release test to ensure that neurovirulence of chimeras does not exceed that of the virus vector (YF-VAX®) used to construct ChimeriVax™ viruses. Because all chimeras constructed so far (with or without mutations) are not virulent for adult mice (3-4 weeks old), these animals cannot be used to identify subtle changes in neurovirulence of chimeras associated with single amino acid substitutions. In contrast, suckling mice of 4-10 days of age are more sensitive to minor changes in the genome of chimeras, which are involved in virulence. In the course of development of ChimeriVax™-DEN viruses, several mutations were observed across the genome of all 4 chimeras (Guirakhoo et al., J. Virol. 75:7290-7304, 2001). These mutations were corrected in all chimeras, and the reconstructed viruses (except for DEN1 chimeras) were successfully evaluated for safety and immunogenicity in monkeys. Due to instability of DEN1 plasmids, the reconstruction of this chimera (without mutation) was not accomplished on time, and could therefore not be tested in monkeys. During plaque purification to produce a PMS for DEN1 chimera, 10 different clones (A-J) were sequenced to identify a clone without mutations (Table 5). All but one clone (J) contained 1 or 2 mutations within the envelope protein E. Representative clones of DEN1 chimeras were evaluated for their neurovirulence using 4 day-old suckling mice (Table 6). Animals were inoculated by the i.c. route with two 0.02 ml of undiluted, 1:10, or 1:100 dilutions of each chimeric DEN1 virus and observed for 21 days. The actual doses were determined by back titration of inocula in a plaque assay. As is shown in Table 6, all clones except clone E exhibited similar neurovirulence for 4 day-old mice with average survival times (AST) significantly lower than that of YF-VAX® ($p<0.001$ using JMP software, Version 4.0.2). Clone E (E204K>R) was significantly less virulent than all other DEN1 clones ($p<0.0001$). Interestingly, one of the 2 mutations identified in the original DEN1 chimera was the E204 K>R substitution. This virus induced a low level of viremia (mean peak titer 0.7 $\log_{10}$ PFU/ml) for 1.3 days when inoculated into monkeys (Guirakhoo et al., J. Virol. 75:7290-7304, 2001). Clone J, which did not contain any mutations and was shown to be significantly less virulent than YF-VAX® in 4 days old mice, P=0.001, was selected for production of the cGMP MS virus.

Safety and Immunogenicity (Viremia and Neutralizing Antibody Responses) of Chimeric DEN1 Viruses in Monkeys The effect of the E204 mutation on viscerotropism (viremia) of the virus was assessed by inoculation of monkeys with ChimeriVax-DEN1 viruses with (clone E, P6) or without (clone J, P7) the E204 mutation. The original DEN1 chimera (ChimeriVax-DEN-1, uncloned P4, 1999, Group 1) was selected as a control, because its viremia and immunogenicity profiles had already been evaluated in monkeys as a monovalent or a tetravalent (combined with 3 other chimeras) vaccine (Guirakhoo et al., J. Virol. 75:7290-7304, 2001).

Groups of 4 rhesus monkeys were inoculated with 5 $\log_{10}$ PFU/0.5 ml of DEN1 chimeras (Table 7). Viremia was measured (by plaque assay on Vero cells) on sera obtained from Day 2 to Day 11 post infection. All monkeys inoculated with DEN1 PMS virus (Group 3) became viremic, whereas 3/4 and 2/4 monkeys inoculated with clone E or uncloned viruses, respectively, became viremic (Table 8). The mean peak virus titer (2.5 $\log_{10}$ PFU/ml) and duration (8.5 days) of viremia in Group 3 monkeys (DEN1 PMS) was significantly higher ($p=0.024$ and 0.0002 for peak virus titer and duration, respectively) than Groups 1 and 2. Despite the lack of viremia in some monkeys, all animals developed neutralizing antibody titers against homologous viruses. For neutralization assays, sera from each group of monkeys were heat inactivated and mixed with the homologous virus (the same virus that had been used for inoculation of animals in each group). Consistent with the level of viremia, the neutralizing titers in monkeys immunized with the PMS virus (without mutation) were higher than the other 2 groups ($p=0.0002$). The sera of Group 1 monkeys (immunized with a DEN1 chimera with 2 mutations on the envelope proteins, prM and E) revealed the lowest neutralizing titers (Table 9), indicating that the M39 mutation may have further attenuated the virus ($p=0.0045$). These experiments demonstrated that there might be a direct correlation for ChimeriVax™-DEN viruses between 1) the magnitude of viremia and the level of neutralizing antibodies in monkeys, and 2) neurovirulence of chimera for mouse and viremia/immunogenicity in monkeys (clone E was attenuated for 4 days old mice and induced a lower level of viremia and neutralizing antibodies than the PMS virus, which was neurovirulent for mice of similar age).

In summary, the mutation at E204 residue of ChimeriVax™-DEN1 controls the replication of the DEN1 chimera in vertebrate hosts, as shown by viremia and neutralizing responses. Mutation of this residue, which is conserved in all dengue serotypes (Table 10), can thus be used in the construction of chimeras with desired phenotypes appropriate for human dengue vaccine.

TABLE 1

Comparison of the amino acid differences in the E protein of ChimeriVax ™-JE $FRhL_3$ and ChimeriVax ™-JE $FRhL_5$ virus with published sequences of JE SA14-14-2 vaccine, wild-type JE strains, parental SA14, and Nakayama virus. ChimeriVax ™-JE $FRhL_3$ and $FRhL_5$ viruses were sequenced across their entire genomes and the mutation at E279 was the only difference found.

| Virus | E107 | E138 | E176 | E177 | E227 | E244 | E264 | E279 | E315 | E439 |
|---|---|---|---|---|---|---|---|---|---|---|
| ChimeriVax ™-JE $FRhL_3$ E279 Met | F | K | V | A | S | G | H | M | V | R |
| ChimeriVax ™-JE $FRhL_5$ E279 Lys | F | K | V | A | S | G | H | K | V | R |
| JE SA14-14-2 PDK[1] | F | K | V | T | S | G | Q | M | V | R |
| JE SA14-14-2 PHK[2] | F | K | V | A | S | G | H | M | V | R |

TABLE 1-continued

Comparison of the amino acid differences in the E protein of ChimeriVax ™-JE $FRhL_3$ and ChimeriVax ™-JE $FRhL_5$ virus with published sequences of JE SA14-14-2 vaccine, wild-type JE strains, parental SA14, and Nakayama virus. ChimeriVax ™-JE $FRhL_3$ and $FRhL_5$ viruses were sequenced across their entire genomes and the mutation at E279 was the only difference found.

| Virus | E107 | E138 | E176 | E177 | E227 | E244 | E264 | E279 | E315 | E439 |
|---|---|---|---|---|---|---|---|---|---|---|
| JE SA14[1,3] | L | E | I | T | S | G | Q | K | A | K |
| JE Nakayama[4] | L | E | I | T | P | E | Q | K | A | K |

[1]Nitayaphan S. et al. 1990. Virology 177: 541-552

[2]Ni H. et al. 1994. J. Gen. Virol. 75: 1505-1510; PDK = primary dog kidney

[3]Aihara S. et al. 1991. Virus Genes 5: 95-109; PHK = primary hamster kidney

[4]McAda P. et al. 1987. Virology 158: 348-360

TABLE 2

Neurovirulence for suckling mice of ChimeriVax ™-JE viruses with and without a mutation at E279 and YF 17D vaccine

| Experiment | Mouse age (days) | Virus, passage and E279 amino acid | Intracerebral dose ($Log_{10}$ PFU) | Mortality (%) | Average Survival Time (Days) | $LD_{50}$ ($Log_{10}$ PFU) |
|---|---|---|---|---|---|---|
| 1 | 8.6 | YF-VAX ® | 1.15 | 10/10 (100) | 8.4 | 0.11 |
| | | | 0.15 | 5/10 (50) | 10 | |
| | | | 0-0.85 | 1/10 (10) | 14 | |
| | | ChimeriVax ™- | 2.60 | 1/10 (10) | 15 | >2.6 |
| | | JE, $FRhL_3$, | 1.6 | 1/10 (10) | 13 | |
| | | E279 Met | 0.6 | 0/10 (0) | N/A | |
| | | | −0.45 | 0/10 (0) | N/A | |
| | | ChimeriVax ™- | 3.0 | 10/10 (100) | 10.3 | 1.64 |
| | | JE, $FRhL_5$, | 2.0 | 8/10 (80) | 11.25 | |
| | | E279 Lys | 1.0 | 2/10 (20) | 14.5 | |
| | | | 0 | 2/10 (20) | 16 | |
| 2 | 4 | YF-VAX ® | 0.95 | 11/11 (100) | 8.4 | −0.3 |
| | | | −0.05 | 9/11 (82) | 8.8 | |
| | | | −1.05 | 2/12 (17) | 10 | |
| | | ChimeriVax ™- | 2.69 | 7/12 (58) | 10.6 | 2.5 |
| | | JE, $FRhL_3$, | 1.69 | 4/12 (33) | 11.5 | |
| | | E279 Met | 0.69 | 0/12 (0) | NA | |
| | | ChimeriVax ™- | 2.88 | 10/12 (83) | 9.3 | 1.45 |
| | | JE, $FRhL_5$, | 1.88 | 11/12 (92) | 10.3 | |
| | | E279 Lys | 0.88 | 4/12 (33) | 12.2 | |
| | | | −0.11 | 2/12 (17) | 14 | |
| | | | −1.11 | 0/12 (0) | NA | |
| | | $YF/JE_{279}$ site- | 3.55 | 12/12 (100) | 9.4 | 1.15 |
| | | specific | 2.55 | 11/12 (92) | 10.1 | |
| | | revertant, | 1.55 | 11/12 (92) | 10.2 | |
| | | E279 Lys | 0.55 | 3/12 (25) | 10.7 | |
| | | | −0.44 | 2/12 (17) | 14 | |

TABLE 3

Neuropathological evaluation, monkeys inoculated IC with ChimeriVax ™-JE $FRhL_3$, $FRhL_5$ or yellow fever 17D (YF-VAX ®) and necropsied on day 30 post-inoculation.

| | | | Dose[1] | Clinical score[2] | Individual and group mean histopathological score | | |
|---|---|---|---|---|---|---|---|
| Test virus | Monkey | Sex | $log_{10}$ PFU/ 0.25 mL | Maximum score/Mean daily score | Target area[3] | Discriminator areas[4] | Target + Discriminator areas |
| YF-VAX ® | RT702M | M | 4.05 | 1/0 | 2.00 | 0.51 | 1.26 |
| Connaught | RT758M | M | 4.28 | 1/0 | 0.25 | 0.01 | 0.13 |
| Lot # 0986400 | RT653M | M | 4.07 | 1/0 | 2.00 | 0.39 | 1.20 |
| | RT776M | M | 4.25 | 3/1 | 2.00 | 1.29 | 1.65 |
| | RT621M | M | 4.34 | 3/2 | 1.00 | 0.46 | 0.73 |
| | RAH80F | F | 4.14 | 3/1 | 1.50 | 0.71 | 1.10 |
| | RAL02F | F | 4.13 | 1/1 | 2.00 | 0.80 | 1.40 |
| | RT698F | F | 3.78 | 3/1 | 1.50 | 0.64 | 1.07 |

TABLE 3-continued

Neuropathological evaluation, monkeys inoculated IC with ChimeriVax ™-JE $FRhL_3$, $FRhL_5$ or yellow fever 17D (YF-VAX ®) and necropsied on day 30 post-inoculation.

| | | | Dose[1] | Clinical score[2] | Individual and group mean histopathological score | | |
|---|---|---|---|---|---|---|---|
| Test virus | Monkey | Sex | $log_{10}$ PFU/ 0.25 mL | Maximum score/Mean daily score | Target area[3] | Discriminator areas[4] | Target + Discriminator areas |
| | RAI12F | F | 4.11 | 1/1 | 2.00 | 1.45 | 1.73 |
| | RP942F | F | 4.05 | 1/0 | 2.00 | 0.81 | 1.41 |
| | Mean | | 4.12 | 1 | 1.63 | 0.71 | 1.17 |
| | SD | | 0.16 | 1 | 0.59 | 0.42 | 0.47 |
| ChimeriVax ™-JE, $FRhL_3$ Lot# I031299A | RT452M | M | 3.55 | 1/0 | 0.50 | 0.08 | 0.29 |
| | RR257M | M | 3.52 | 1/0 | 1.00 | 0.14 | 0.57 |
| | RT834M | M | 3.71 | 1/0 | 0.50 | 0.38 | 0.44 |
| | RT620M | M | 3.71 | 1/0 | 1.00 | 0.14 | 0.57 |
| | RT288M | M | 3.76 | 1/0 | 0.50 | 0.19 | 0.35 |
| | RAJ98F | F | 3.79 | 1/1 | 0.00 | 0.11 | 0.05 |
| | RAR08F | F | 3.52 | 1/0 | 0.00 | 0.13 | 0.07 |
| | RV481F | F | 3.52 | 1/0 | 0.00 | 0.06 | 0.03 |
| | RT841F | F | 3.71 | 1/0 | 0.50 | 0.05 | 0.28 |
| | RT392F | F | 3.76 | 1/0 | 0.50 | 0.07 | 0.29 |
| | Mean | | 3.66 | 0 | 0.45 | 0.14 | 0.29 |
| | SD | | 0.11 | 0 | 0.37 | 0.10 | 0.20 |
| P-value (t Test[5]) vs. YF-VAX ® | | | | 0.037/0.025 | 0.00008 | 0.00191 | 0.00014 |
| ChimeriVax ™-JE, $FRhL_5$ Lot # 99B01 | RT628M | M | 4.20 | 1/0 | 0.50 | 0.57 | 0.54 |
| | RT678M | M | 4.19 | 1/0 | 1.00 | 0.12 | 0.60 |
| | RT581M | M | 4.17 | 1/0 | 1.00 | 0.46 | 0.73 |
| | RR726M | M | 4.32 | 1/0 | 1.00 | 0.66 | 0.83 |
| | RR725M | M | ND[6] | 1/0 | 1.00 | 0.33 | 0.67 |
| | RAJ55F | F | 4.27 | 0/0 | 1.00 | 0.14 | 0.57 |
| | RT769F | F | 4.44 | 1/0 | 1.00 | 0.58 | 0.79 |
| | RAK22F | F | 4.24 | 1/0 | 0.00 | 0.12 | 0.06 |
| | RT207F | F | 4.49 | 1/1 | 1.00 | 0.22 | 0.61 |
| | RT490F | F | 4.34 | 1/0 | 0.00 | 0.04 | 0.02 |
| | Mean | | 4.30 | 0 | 0.75 | 0.32 | 0.54 |
| | SD | | 0.11 | 0 | 0.42 | 0.23 | 0.28 |
| P-value (t Test) vs. YF-VAX ® | | | | 0.024/0.025 | 0.00154 | 0.02436 | 0.00248 |
| P-value (t Test) vs. ChimeriVax ™-JE $FRhL_3$ | | | | 0.343/1.00 | 0.10942 | 0.03223 | 0.03656 |

[1]Back-titration

[2]Clinical score: 0 = no signs; 1 = rough coat, not eating; 2 = high pitched voice, inactive, slow moving; 3 = tremor, incoordination, shaky movements, limb weakness; 4 = inability to stand, paralysis, moribund, or dead. The maximum score on any day and the mean score over the 30-day observation period are shown.

[3]Substantia nigra

[4]Corpus striatum and thalamus, right and left side (N. caudatus, globus pallidus, putamen, N. ant./lat. thalami, N. lat. thalami; cervical and lumbar enlargements of the spinal cord (6 levels)

[5]Student's t test, two-sided, heteroscedastic, comparing YF-VAX ® and ChimeriVax ™-JE viruses.

[6]Not done

TABLE 4

Viremia, rhesus monkeys inoculated IC with YF-VAX ® or ChimeriVax ™-JE $FRHL_3$ and $FRHL_5$ viruses (for dose inoculated, see Table 3)

| | Serum Virus Titer ($Log_{10}$ PFU/mL), Day | | | | | | | | |
|---|---|---|---|---|---|---|---|---|---|
| Animal | 1 | 2 | 3 | 4 | 5 | 6 | 7 | 8 | 9 |
| YF-VAX ® Control | | | | | | | | | |
| RT702M | —[1] | — | 1.6 | 3.0 | — | — | — | — | — |
| RAH80F | — | — | — | 3.3 | 2.5 | — | — | — | — |
| RT758M | — | — | 2.1 | 3.2 | 2.8 | — | — | — | — |
| RAL02F | — | — | — | 1.3 | — | — | — | — | — |
| RT653M | — | — | — | 2.7 | — | — | — | — | — |
| RT698F | — | 1.0 | 2.3 | 3.7 | 2.5 | — | 1.0 | — | — |
| RT776M | — | — | — | — | — | — | — | — | — |
| RAI12F | — | — | — | 2.0 | 2.5 | 2.5 | 2.0 | — | — |
| RT621M | — | 1.0 | 2.0 | 3.3 | 2.0 | — | — | — | — |
| RP942F | — | 1.0 | 2.6 | 3.6 | 2.0 | — | — | — | — |
| Mean Titer[2] | | 0.8 | 1.4 | 2.7 | 1.7 | 0.9 | 0.9 | | |
| SD | | 0.1 | 0.8 | 1.0 | 0.9 | 0.6 | 0.4 | | |
| ChimeriVax ™-JE $FRHL_3$ E279 Met | | | | | | | | | |
| RAJ98F | — | — | 1.9 | 1.3 | — | — | — | — | — |
| RT452M | — | 1.3 | 2.1 | 1.6 | — | — | — | — | — |

TABLE 4-continued

Viremia, rhesus monkeys inoculated IC with YF-VAX ® or ChimeriVax ™-JE $FRHL_3$ and $FRHL_5$ viruses (for dose inoculated, see Table 3)

| Animal | Serum Virus Titer ($Log_{10}$ PFU/mL), Day 1 | 2 | 3 | 4 | 5 | 6 | 7 | 8 | 9 |
|---|---|---|---|---|---|---|---|---|---|
| RAR08F | — | — | 1.3 | 2.2 | 2.2 | 1.8 | — | — | — |
| RR257M | — | — | 1.9 | 2.2 | 1.8 | — | — | — | — |
| RV481F | — | — | 2.1 | 1.8 | 1.5 | — | — | — | — |
| RT834M | — | — | 2.5 | 1.3 | — | — | — | — | — |
| RT841F | — | — | 2.4 | 1.7 | — | — | — | — | — |
| RT620M | — | — | 1.6 | 1.0 | — | — | — | — | — |
| RT392F | — | — | — | — | — | — | — | — | — |
| RT288M | — | — | — | — | — | — | — | — | — |
| Mean Titer | | 0.8 | 1.7 | 1.5 | 1.0 | 0.8 | | | |
| SD | | 0.2 | 0.6 | 0.5 | 0.6 | 0.3 | | | |
| P-value[3] | | 0.696 | 0.386 | 0.003 | 0.065 | 0.745 | | | |
| ChimeriVax ™-JE $FRhL_5$ E279 Lys | | | | | | | | | |
| RT628M | — | — | — | — | — | — | — | — | — |
| RAJ55F | — | — | — | — | — | — | — | — | — |
| RT678M | — | — | — | — | — | — | — | — | — |
| RT769F | — | — | — | 2.0 | — | — | — | — | — |
| RT581M | — | — | — | — | — | — | — | — | — |
| RAK22F | — | — | — | — | — | — | 1.8 | — | — |
| RR726M | — | — | — | — | — | — | — | — | — |
| RT207F | — | — | — | — | — | — | — | — | — |
| RR725M | — | — | — | — | — | — | — | — | — |
| RT490F | — | — | — | — | — | — | — | — | — |
| Mean Titer | | 0.7 | 0.7 | 0.8 | 0.7 | 0.7 | 0.8 | | |
| SD | | 0.0 | 0.0 | 0.4 | 0.0 | 0.0 | 0.4 | | |
| P-value[4] | | 0.331 | <0.000 | 0.010 | 0.076 | 1.0 | 1.0 | | |

[1]— = No detectable viremia; in most tests neat serum was tested, the cutoff being 1.0 $log_{10}$ PFU/mL); in some cases, neat serum was toxic to cells, and serum diluted 1:2 or 1:5 was used (cut-off 1.3 or 1.7 $log_{10}$ PFU/mL).
[2]For the purpose of calculating mean titers and standard deviations, 0.7 was used in place of <1.0, 1.0 was used in place of <1.3, and 1.4 was used in place of <1.7.
[3]Comparison with YF-VAX ® by t-test, 2-tailed
[4]Comparison with ChimeriVax ™JE $FRhL_3$ by t-test, 2-tailed

TABLE 5

Nucleotide and amino acid sequences of uncloned and various clones of ChimeriVax-DEN1 viruses and their in vitro (Vero passages) genetic stabilities.

| Virus | Passage | Gene | Nt. No[a] | Nt. change/ heterogeneity | AA change/ heterogeneity | AA No[b] | Comments |
|---|---|---|---|---|---|---|---|
| Uncloned | P2 | — | — | — | — | — | No mutations |
| **Uncloned** | **P5** | **E** | **1590** | **A/G** | **K/R** | **204** | **Nucleotide heterogeneity** |
| | | **E** | **1730** | **G/T** | **V/F** | **251** | **Nucleotide heterogeneity** |
| | | **E** | **1912** | **G/t** | **E/D** | **311** | **Barely detectable mutant** |
| | | **E** | **2282** | **C/a** | **L/I** | **435** | **Undetectable mutants in some samples** |
| **Uncloned** | **P15** | **E** | **1590** | **A to G** | **K to R** | **204** | |
| | | **NS2B** | **4248** | **G to T** | **G to V** | | |
| | | **NS4A** | **6888** | **C/T** | **A/V** | | **Nucleotide heterogeneity** |
| | | **NS4A** | **7237** | **A/G** | **I/M** | | **Nucleotide heterogeneity** |
| **Uncloned** | **P15** | **E** | **1590** | **A to G** | **K to R** | **204** | |
| | **REPEAT** | **E** | **1730** | **G/T** | **V/F** | **251** | **Nucleotide heterogeneity** |
| | **from P2** | **NS4A** | **7237** | **A/G** | **I/M** | **263** | **Nucleotide heterogeneity** |
| | | **NS4B** | **7466** | **C/t** | **P/S** | **52** | **Barely detectable mutant** |
| Clone A | P3, P7 | E | 1730 | G to T | V to F | 251 | Domain II j strand, no function assigned |
| | | E | 2282 | C to A | L to I | 435 | Before anchor; L and I in D2 and YF respectively. (a gap left, nt 7080-7220) |
| Clone B | P3, P7, P10 | E | 1730 | G to T | V to F | 251 | |
| Clone C | P3, P6 | E | 1912 | G to T | E to D | 311 | Domain III, a strand, no function assigned. |
| Clone D | P3, P6 | E | 1730 | G to T | V to F | 251 | |
| **Clone E** | **P3, P6** | **E** | **1590** | **A to G** | **K to R** | **204** | **Domain II, f-g loop of, no function ass.** |
| **Clone F** | **P3** | **M** | **788** | **C to T** | **—** | **—** | |
| | | **E** | **1590** | **A to G** | **K to R** | **204** | |
| Clone G | P3 | E | 1730 | G to T | V to F | 251 | |
| Clone H | P3 | E | 1912 | G to T | E to D | 311 | |
| | | E | 2030 | G to T | V to L | 351 | Domain III, d strand (L in D2 and D3; I in D4) |

TABLE 5-continued

Nucleotide and amino acid sequences of uncloned and various clones of ChimeriVax-DEN1 viruses and their in vitro (Vero passages) genetic stabilities.

| Virus | Passage | Gene | Nt. No[a] | Nt. change/ heterogeneity | AA change/ heterogeneity | AA No[b] | Comments |
|---|---|---|---|---|---|---|---|
| **Clone I** | **P3** | **E** | **1590** | **A to G** | **K to R** | **204** | |
| Clone J (J-2) | P3, P6, P7, P10 | — | — | — | — | — | |
| **Cline J (J-2)** | **P8 (cGMP MS)** | **E** | **1590** | **A to G (a/G)** | **K to R** | **204** | **Some parent (a) nucleotide still present** |
| | **P10 from (cGMP MS)** | **E** | **1590** | **A to G** | **K to R** | **204** | |
| **Clone J (J-2)** | **P10 REPEAT from P7** | **E** | **1590** | **A to G** | **K to R** | **204** | |
| **Clone J (J-2)** | **P20 From P10 repeat** | **E** | **1590** | **A to G** | **K to R** | **204** | |
| | | **NS4A** | **6966** | **G/T** | **S/I** | **171** | |
| | | **NS4A** | **7190** | **G/a** | **V/I** | **246** | |

[a]From the beginning of the genome.
[b]From the N-terminus of indicated protein; numbering according to Rice et al., Science 229: 726-733, 1985. Clones with 204 mutations are shown in bold letters.

TABLE 6

Neurovirulence of different clones of chimeric DEN1 viruses in 4-day old suckling mice.

| ChimeriVax-DEN1 | Mutation | Dilution | Dose (BT) | No. dead/total (% dead) | AST Days |
|---|---|---|---|---|---|
| Uncloned | None | Neat | 5.0 | 11/11 (100) | 9.1 |
| (P2) | | 1:10 | 4.1 | 11/11 (100) | 10.2 |
| Clone B | E251 | Neat | 5.8 | 10/11 (91) | 9.8 |
| (P7) | V to F | 1:10 | 5.0 | 11/11 (100) | 10.2 |
| Clone C | E311 | Neat | 5.8 | 11/11 (100) | 8.5 |
| (P6) | E to D | 1:10 | 4.9 | 11/11 (100) | 9.5 |
| Clone E | E204 | Neat | 5.9 | 3/11 (27) | 13 |
| (P6) | K to R | 1:10 | 4.8 | 1/11 (9) | 14 |
| | | 1:100 | 4.0 | 1/11 (9) | 15 |
| Clone J | None | Neat | 3.6 | 11/11 (100) | 10.8 |
| (P3) | | 1:10 | 3.0 | 11/11 (100) | 11.3 |
| | | 1:100 | 1.8 | 9/11 (82) | 11.3 |
| YF-VAX ® | NA | 1:20 | 2.5 | 12/12 (100) | 8.3 |

TABLE 7

Immunogenicity Study in Rhesus Monkeys, ChimeriVax ™-DEN1 viruses, Sierra Biomedical NON-GLP Study

| Group* | Virus | Mutation | Dose (0.5 ml) |
|---|---|---|---|
| 1 | ChimeriVax-DEN-1 Uncloned, P4, 1999** | M39 and E204 | 5 logs |
| 2 | ChimeriVax-DEN-1, P6, clone E | E204 | 5 logs |
| 3 | ChimeriVax-DEN-1, PMS (P7), clone J | None | 5 logs |

*Four monkeys (2M/2F) per group.
**Guirakhoo et al 2001

TABLE 8

Viremia in monkeys immunized with 5 $log_{10}$ PFU (S.C.) of different clones of ChimeriVax-DEN1 viruses

| Monkey | Virus (Mutation) | Viremia ($log_{10}$ PFU/ml) by post-immunization day: 2* | 3 | 4 | 5 | 6 | 7 | 8 | 9 | 10 | 11 |
|---|---|---|---|---|---|---|---|---|---|---|---|
| R18265M | ChimeriVax ™-DEN1, 99, P4, uncloned (M39, E204) | —** | — | — | — | — | — | — | — | — | — |
| R175110F | | — | — | — | 1.7 | — | — | — | — | — | — |
| R17572M | | 1.3 | 1.0 | — | 1.0 | — | — | — | — | — | — |
| R171114F | | — | — | — | — | — | — | — | — | — | — |
| R182103M | ChimeriVax ™-DEN1, P6, clone E, (E204) | — | — | — | — | — | — | — | — | — | — |
| R17098F | | — | 1.7 | — | — | — | — | — | — | — | — |
| R18261M | | 1.7 | 2.5 | 1.3 | 2.0 | | | | | | — |
| R175118F | | — | — | 1.0 | — | — | — | — | — | — | — |
| R182104M | ChimeriVax ™-DEN1, P7, clone J, PMS (None) | 1.0 | 1.9 | 1.7 | 1.7 | 1.8 | 1.7 | 1.0 | 1.0 | 1.7 | — |
| R175108F | | — | 1.7 | 2.8 | 2.2 | 1.0 | 2.0 | 1.7 | 2.0 | 2.2 | 1.7 |
| R182111M | | 2.3 | 3.0 | 3.3 | 2.8 | 1.7 | 1.7 | — | — | — | — |
| R175104F | | — | 2.4 | 1.3 | 2.0 | 2.3 | 1.7 | 1.7 | 2.2 | 3.0 | 3.1 |

*Monkeys were immunized on Day 1.
**<1.0 log10 PFU/ml

TABLE 9

Viremia and neutralizing antibody titers (50%) in monkeys immunized with 5 $log_{10}$ PFU (S.C.) of different clones of ChimeriVax-DEN1 viruses

| Monkey | Mutation | No. viremic/no. tested (%) | Mean Peak titer | Mean Duration | Neut. Ab titer | Plaque size (mm) |
|---|---|---|---|---|---|---|
| R18265M | YF-DEN1, 99, | 2/4 (50) | 1.5 | 1.5 | 640 | 2-4 |
| R175110F | P4, uncloned | | | | 640 | |
| R17572M | (M39, E204) | | | | 320 | |
| R171114F | | | | | 640 | |
| R182103M | YF-DEN1, 01, | 3/4 (75) | 1.7 | 2 | 5120 | 2-4 |
| R17098F | P6, clone E | | | | 2560 | |
| R18261M | (E204) | | | | 2560 | |
| R175118F | | | | | 5120 | |
| R182104M | YF-DEN1, 01, | 4/4 (100) | 2.5 | 8.5 | 5120 | 1 |
| R175108F | P7, clone J, | | | | 10240 | |
| R182111M | PMS | | | | 10240 | |
| R175104F | (None) | | | | 10240 | |

TABLE 10

Position of 204 residues in ChimeriVax ™-DEN1-4 E proteins

| ChimeriVax- | Amino Acid residues, E protein 200 | 201 | 202 | 203 | 204 | 205 | 206 | 207 | 208 |
|---|---|---|---|---|---|---|---|---|---|
| DEN1 | T | M | K | E | **K** | S | W | L | V |
| DEN2 | Q | M | E | N | **K** | A | W | L | V |
| DEN3 | T | M | K | N | **K** | A | W | M | V |
| DEN4 | K | M | K | K | **K** | T | W | L | V |

What is claimed is:

1. A method of reducing the viscerotropism and/or neurovirulence of a flavivirus which is a chimeric flavivirus comprising sequences encoding capsid and non-structural proteins of a first flavivirus and pre-membrane and envelope proteins of a dengue virus selected from a dengue-1 virus, a dengue-2 virus, a dengue-3 virus, and a dengue-4 virus, the method comprising substituting lysine at envelope protein position 202 (dengue-3) or 204 (dengue-1, dengue-2, or dengue-4) with arginine.

2. The method of claim 1, wherein said sequences encoding said dengue pre-membrane and envelope proteins encode pre-membrane and envelope proteins of a dengue-1 virus.

3. The method of claim 1, wherein said sequences encoding said dengue pre-membrane and envelope proteins encode pre-membrane and envelope proteins of a dengue-2 virus.

4. The method of claim 1, wherein said sequences encoding said dengue pre-membrane and envelope proteins encode pre-membrane and envelope proteins of a dengue-3 virus.

5. The method of claim 1, wherein said sequences encoding said dengue pre-membrane and envelope proteins encode pre-membrane and envelope proteins of a dengue-4 virus.

6. The method of claim 1, wherein said first flavivirus is a yellow fever virus.

7. The method of claim 6, wherein said substitution reduces the viscerotropism of said chimeric flavivirus.

8. A method of inducing an immune response to a flavivirus in a subject, said method comprising administering to said patient a flavivirus which is a chimeric flavivirus comprising sequences encoding capsid and non-structural proteins of a first flavivirus and pre-membrane and envelope proteins of a dengue virus selected from a dengue-1 virus, a dengue-2 virus, a dengue-3 virus and a dengue-4 virus, wherein the dengue virus envelope protein has a substitution of the lysine at amino acid position 202 (dengue-3) or 204 (dengue-1, dengue-2, or dengue-4) with arginine and wherein said method results in decreased viscerotropism and/or neurovirulence in said subject relative to a corresponding flavivirus lacking the substitution.

9. The method of claim 8, wherein said sequences encoding said dengue pre-membrane and envelope proteins encode pre-membrane and envelope proteins of a dengue-1 virus.

10. The method of claim 8, wherein said sequences encoding said dengue pre-membrane and envelope proteins encode pre-membrane and envelope proteins of a dengue-2 virus.

11. The method of claim 8, wherein said sequences encoding said dengue pre-membrane and envelope proteins encode pre-membrane and envelope proteins of a dengue-3 virus.

12. The method of claim 8, wherein said sequences encoding said dengue pre-membrane and envelope proteins encode pre-membrane and envelope proteins of a dengue-4 virus.

13. The method of claim 8, wherein said first flavivirus is a yellow fever virus.

14. The method of claim 13, wherein said substitution reduces the viscerotropism of said chimeric flavivirus.

15. The method of claim 8, further comprising administering to said subject three additional chimeric flaviviruses that each comprise sequences encoding capsid and nonstructural proteins of said first flavivirus and pre-membrane and envelope proteins of one of dengue-1, dengue-2, dengue-3, and dengue-4 viruses, wherein the dengue virus sequences of the three additional chimeric flaviviruses are of serotypes that are different from one another and different from that administered in the method of claim 8, and optionally the dengue virus envelope protein of one or more of the three additional chimeras has a substitution of the lysine at amino acid position 202 (dengue-3) or 204 (dengue-1, dengue-2, or dengue-4) with arginine.

16. A method of reducing the viscerotropism and/or neurovirulence of a flavivirus which is a dengue virus selected from a dengue-1 virus, a dengue-2 virus, a dengue-3 virus, and a dengue-4 virus, the method comprising substituting lysine at envelope protein position 202 (dengue-3) or 204 (dengue-1, dengue-2, or dengue-4) with arginine, wherein when viscerotropism and/or neurovirulence of said dengue-3 virus is reduced, said substitution of lysine at envelope protein position 202 with arginine is the only mutation in said dengue-3 virus.

17. The method of claim 16, wherein said dengue virus is a dengue-1 virus.

18. The method of claim 16, wherein said dengue virus is a dengue-2 virus.

19. The method of claim 16, wherein said dengue virus is a dengue-3 virus.

20. The method of claim 16, wherein said dengue virus is a dengue-4 virus.

21. The method of claim 16, wherein said substitution reduces the viscerotropism of said flavivirus.

22. A method of inducing an immune response to a flavivirus in a subject, said method comprising administering to said patient a flavivirus which is a dengue virus selected from a dengue-1 virus, a dengue-2 virus, a dengue-3 virus, and a dengue-4 virus, wherein the dengue virus envelope protein has a substitution of the lysine at amino acid position 202 (dengue-3) or 204 (dengue-1, dengue-2 or dengue-4) with arginine and wherein said method results in decreased viscerotropism and/or neurovirulence in said subject relative to a corresponding flavivirus lacking the substitution.

23. The method of claim 22, wherein said dengue virus is a dengue-1 virus.

24. The method of claim 22, wherein said dengue virus is a dengue-2 virus.

25. The method of claim 22, wherein said dengue virus is a dengue-3 virus.

26. The method of claim 22, wherein said dengue virus is a dengue-4 virus.

27. The method of claim 22, wherein said substitution reduces the viscerotropism of said flavivirus.

* * * * *